(12) United States Patent
Asgeirsson et al.

(10) Patent No.: US 11,390,025 B2
(45) Date of Patent: Jul. 19, 2022

(54) MEDICAL DEVICE INCLUDING A STRUCTURE BASED ON FILAMENTS

(71) Applicant: Ossur Iceland ehf, Reykjavik (IS)

(72) Inventors: Sigurdur Asgeirsson, Foothill Ranch, CA (US); Jiri Dlab, Foothill Ranch, CA (US); Larus Sigfusson, Foothill Ranch, CA (US); Rowan Cain, Reykjavik (IS); Stefan Orn Stefansson, Reykjavik (IS); Andri Orrason, Reykjavik (IS); Linda Ros Birgisdottir, Reykjavik (IS); Hogna Hringsdottir, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 150 days.

(21) Appl. No.: 16/680,959

(22) Filed: Nov. 12, 2019

(65) Prior Publication Data

US 2020/0146850 A1    May 14, 2020

Related U.S. Application Data

(60) Provisional application No. 62/760,030, filed on Nov. 12, 2018, provisional application No. 62/759,237, filed on Nov. 12, 2018.

(51) Int. Cl.
*A61F 2/78* (2006.01)
*B29C 64/209* (2017.01)
(Continued)

(52) U.S. Cl.
CPC ........ *B29C 64/209* (2017.08); *A61F 2/30907* (2013.01); *A61F 2/7812* (2013.01);
(Continued)

(58) Field of Classification Search
CPC .............. A61F 2/80; A61F 2002/30909; A61F 2250/0076; A61F 2/30907; A61F 2/7812;
(Continued)

(56) References Cited

U.S. PATENT DOCUMENTS 529,719 A    11/1894    Eils
541,275 A    6/1895    Hepp
(Continued)

FOREIGN PATENT DOCUMENTS

AT    6615 U1    1/2004
CA    2398059 A1    8/2001
(Continued)

OTHER PUBLICATIONS

Klute et al., "Prosthetic Liners for Lower Limb Amputees: A Review of the Literature," Prosthetics and Orthotics International, vol. 34, No. 2, Jun. 2010, pp. 146-153.
(Continued)

*Primary Examiner* — Jerrah Edwards
*Assistant Examiner* — Aren Patel
(74) *Attorney, Agent, or Firm* — Workman Nydegger

(57) ABSTRACT

A lattice or solid structure for a medical device includes a first layer of first filaments discretely formed from at least one medical-grade silicone material. The first filaments are arranged in a predetermined pattern and may be directly adjacent to one another or spaced apart. Additional layers of filaments may be provided adjacent to the first layer, and chemically bonded thereto to form an integrated structure that is without interruption or with interstices therebetween.

22 Claims, 12 Drawing Sheets

(51) Int. Cl.

| | | |
|---|---|---|
| *B29C 64/118* | (2017.01) | |
| *B29C 64/245* | (2017.01) | |
| *B29C 64/255* | (2017.01) | |
| *B29C 64/295* | (2017.01) | |
| *B29C 64/343* | (2017.01) | |
| *B29C 64/227* | (2017.01) | |
| *A61F 2/30* | (2006.01) | |
| *A61F 2/80* | (2006.01) | |
| *B33Y 30/00* | (2015.01) | |
| *B33Y 40/00* | (2020.01) | |

(52) U.S. Cl.
CPC .............. *A61F 2/80* (2013.01); *B29C 64/118* (2017.08); *B29C 64/227* (2017.08); *B29C 64/245* (2017.08); *B29C 64/255* (2017.08); *B29C 64/295* (2017.08); *B29C 64/343* (2017.08); *A61F 2002/30919* (2013.01); *A61F 2002/7818* (2013.01); *A61F 2002/7837* (2013.01); *A61F 2250/0076* (2013.01); *B33Y 30/00* (2014.12); *B33Y 40/00* (2014.12)

(58) Field of Classification Search
CPC .... A61F 2002/7818; A61F 2002/30919; A61F 2002/7837; B29C 64/209; B29C 64/118; B29C 64/245; B29C 64/255; B29C 64/295; B29C 64/343; B29C 64/227; B29C 64/241; B29C 64/106; B29C 64/336; B29C 64/307; B29C 64/112; B33Y 30/00; B33Y 40/00; B29K 2021/00
See application file for complete search history.

(56) References Cited

U.S. PATENT DOCUMENTS

| | | |
|---|---|---|
| 2,104,742 A | 1/1938 | Fleischer |
| 2,414,716 A | 1/1947 | Carson |
| 2,490,586 A | 12/1949 | Embree |
| 2,680,501 A | 6/1954 | Cunningham |
| 2,765,159 A | 10/1956 | Garofalo |
| 3,019,552 A | 2/1962 | Schleich |
| 3,081,514 A | 3/1963 | Griswold |
| 3,125,195 A | 3/1964 | Moore |
| 3,389,451 A | 6/1968 | Speca et al. |
| 3,391,048 A | 7/1968 | Dyer et al. |
| 3,468,748 A | 9/1969 | Bassett |
| 3,661,670 A | 5/1972 | Pierpont, Jr. |
| 4,107,870 A | 8/1978 | Ausnit |
| 4,205,152 A | 5/1980 | Mizuguchi et al. |
| 4,290,170 A | 9/1981 | Brookstein et al. |
| 4,575,330 A | 3/1986 | Hull |
| 4,674,580 A | 6/1987 | Schuh et al. |
| 4,735,418 A | 4/1988 | Engel |
| 4,777,859 A | 10/1988 | Plummer, Jr. |
| 4,867,834 A | 9/1989 | Alenskis et al. |
| 4,978,564 A | 12/1990 | Douglas |
| 5,045,147 A | 9/1991 | Benson et al. |
| 5,156,629 A | 10/1992 | Shane et al. |
| 5,281,181 A | 1/1994 | McCollum |
| 5,288,287 A | 2/1994 | Castillo et al. |
| 5,372,283 A | 12/1994 | Schmitkons et al. |
| 5,387,245 A | 2/1995 | Fay et al. |
| 5,571,208 A | 11/1996 | Caspers |
| 5,594,652 A | 1/1997 | Penn et al. |
| 5,603,122 A | 2/1997 | Kania |
| 5,702,489 A | 12/1997 | Slemker |
| 5,781,652 A | 7/1998 | Pratt |
| 5,853,313 A | 12/1998 | Zheng |
| 5,888,216 A | 3/1999 | Haberman |
| 5,901,060 A | 5/1999 | Schall et al. |
| 5,928,803 A | 7/1999 | Yasuda |
| 6,012,494 A | 1/2000 | Balazs |
| 6,024,712 A | 2/2000 | Iglesias et al. |
| 6,136,039 A | 10/2000 | Kristinsson et al. |
| 6,165,406 A | 12/2000 | Jang et al. |
| 6,176,875 B1 | 1/2001 | Lenker et al. |
| 6,231,616 B1 | 5/2001 | Helmy |
| 6,231,617 B1 | 5/2001 | Fay |
| 6,264,199 B1 | 7/2001 | Schaedel |
| 6,305,769 B1 | 10/2001 | Thayer et al. |
| 6,358,453 B1 | 3/2002 | Slemker et al. |
| 6,463,351 B1 | 10/2002 | Clynch |
| 6,508,842 B1 | 1/2003 | Caspers |
| 6,554,868 B1 | 4/2003 | Caspers |
| 6,592,539 B1 | 7/2003 | Einarsson et al. |
| 6,626,952 B2 | 9/2003 | Janusson et al. |
| 6,630,093 B1 | 10/2003 | Jones |
| 6,645,253 B2 | 11/2003 | Caspers |
| 6,926,742 B2 | 8/2005 | Caspers et al. |
| 6,968,246 B2 | 11/2005 | Watson et al. |
| 6,991,444 B1 | 1/2006 | Laghi |
| 7,007,370 B2 | 3/2006 | Gracias et al. |
| 7,118,602 B2 | 10/2006 | Bjarnason |
| 7,160,612 B2 | 1/2007 | Magill et al. |
| 7,162,322 B2 | 1/2007 | Arbogast et al. |
| 7,169,189 B2 | 1/2007 | Bjarnason et al. |
| 7,216,678 B2 | 5/2007 | Baer |
| 7,225,045 B2 | 5/2007 | Gothait et al. |
| 7,225,050 B2 | 5/2007 | Sutula, Jr. |
| 7,300,619 B2 | 11/2007 | Napadensky et al. |
| 7,351,264 B2 | 4/2008 | Wilson |
| 7,438,843 B2 | 10/2008 | Asgeirsson |
| 7,447,558 B2 | 11/2008 | Pratt |
| 7,500,846 B2 | 3/2009 | Eshed et al. |
| 7,575,807 B1 | 8/2009 | Barvosa-Carter et al. |
| 7,708,709 B2 | 5/2010 | Brewer |
| 7,785,331 B2 | 8/2010 | Leisinger et al. |
| 7,851,122 B2 | 12/2010 | Napadensky |
| 7,862,624 B2 | 1/2011 | Tran |
| 7,867,286 B2 | 1/2011 | Einarsson |
| 8,082,696 B2 | 12/2011 | Oliver et al. |
| 8,142,860 B2 | 3/2012 | Vanmaele et al. |
| 8,246,888 B2 | 8/2012 | Hopkins et al. |
| 8,308,817 B2 | 11/2012 | Egilsson et al. |
| 8,366,789 B2 | 2/2013 | Summit |
| 8,424,249 B2 | 4/2013 | Oliver |
| 8,475,074 B1 | 7/2013 | Henry |
| 8,523,951 B2 | 9/2013 | Kania |
| 8,652,602 B1 | 2/2014 | Dolla |
| 8,668,744 B2 | 3/2014 | McCarthy |
| 8,795,386 B2 | 8/2014 | Pianykh et al. |
| 8,906,113 B2 | 12/2014 | Mosler et al. |
| 8,940,057 B2 | 1/2015 | Asgeirsson |
| 8,992,183 B2 | 3/2015 | Perich et al. |
| 9,002,496 B2 | 4/2015 | Elsey |
| 9,079,337 B2 | 7/2015 | Lipton et al. |
| D744,719 S | 12/2015 | Amarasiriwardena |
| 9,364,348 B2 | 6/2016 | Sandahl |
| 9,398,963 B2 | 7/2016 | King |
| 9,486,333 B2 | 11/2016 | Wang et al. |
| 9,550,327 B2 | 1/2017 | Swanson et al. |
| 9,669,586 B2 | 6/2017 | Page |
| 9,757,256 B2 | 9/2017 | Sandahl |
| 9,814,607 B2 | 11/2017 | Zhe et al. |
| 9,901,451 B2 | 2/2018 | Conway et al. |
| 9,970,140 B2 | 5/2018 | Taninaka et al. |
| 9,993,357 B2 | 6/2018 | Jonsson |
| 9,993,973 B1 | 6/2018 | Barnhart |
| 10,005,235 B2 | 6/2018 | Millar |
| 10,022,917 B2 | 7/2018 | Pax |
| 10,028,845 B2 | 7/2018 | Jonasson et al. |
| 10,064,726 B1 | 9/2018 | Wei |
| 10,076,880 B2 | 9/2018 | Page |
| 10,166,726 B2 | 1/2019 | Fripp et al. |
| 10,286,601 B2 | 5/2019 | Chang |
| 10,513,089 B2 | 12/2019 | Tibbits et al. |
| 10,543,643 B2 | 1/2020 | Sachs et al. |
| 10,549,505 B2 | 2/2020 | Tibbits et al. |
| 10,633,772 B2 | 4/2020 | Tibbits et al. |
| 2002/0043950 A1 | 4/2002 | Yim et al. |
| 2002/0104973 A1 | 8/2002 | Kerekes |
| 2002/0116847 A1 | 8/2002 | Yen |

(56) References Cited

U.S. PATENT DOCUMENTS

| | | |
|---|---|---|
| 2002/0125790 A1 | 9/2002 | Horning et al. |
| 2003/0090034 A1 | 5/2003 | Mülhaupt et al. |
| 2003/0177749 A1 | 9/2003 | Jen |
| 2003/0181990 A1 | 9/2003 | Phillips |
| 2004/0030411 A1 | 2/2004 | Caspers |
| 2004/0098136 A1 | 5/2004 | Caspers |
| 2004/0137178 A1 | 7/2004 | Janusson et al. |
| 2004/0143345 A1 | 7/2004 | Caspers |
| 2004/0197519 A1 | 10/2004 | Elzey et al. |
| 2004/0244309 A1 | 12/2004 | Raue |
| 2004/0260402 A1 | 12/2004 | Baldini et al. |
| 2005/0101693 A1 | 5/2005 | Arbogast et al. |
| 2005/0119777 A1 | 6/2005 | Arbogast et al. |
| 2005/0149202 A1 | 7/2005 | Schaffer et al. |
| 2005/0227560 A1 | 10/2005 | Allred, III |
| 2006/0016507 A1 | 1/2006 | Baer |
| 2006/0020348 A1 | 1/2006 | Slemker et al. |
| 2006/0159869 A1 | 7/2006 | Kramer et al. |
| 2006/0184231 A1 | 8/2006 | Rucker |
| 2007/0036964 A1 | 2/2007 | Rosenberger et al. |
| 2007/0055383 A1 | 3/2007 | King |
| 2007/0073410 A1 | 3/2007 | Raugel |
| 2007/0106173 A1 | 5/2007 | Korotko et al. |
| 2007/0134486 A1 | 6/2007 | Bansal et al. |
| 2007/0150069 A1 | 6/2007 | Takami et al. |
| 2007/0162154 A1 | 7/2007 | Scott |
| 2007/0163305 A1 | 7/2007 | Baer et al. |
| 2007/0191965 A1 | 8/2007 | Colvin et al. |
| 2008/0027199 A1 | 1/2008 | Mazurek et al. |
| 2008/0039757 A1 | 2/2008 | Nordt, III et al. |
| 2008/0057809 A1 | 3/2008 | Rock |
| 2008/0066393 A1 | 3/2008 | Sorenson |
| 2008/0075850 A1 | 3/2008 | Rock |
| 2008/0075930 A1 | 3/2008 | Kornbluh et al. |
| 2008/0105324 A1 | 5/2008 | Baer |
| 2008/0109103 A1 | 5/2008 | Gershenfeld et al. |
| 2008/0188949 A1 | 8/2008 | Mackenzie |
| 2008/0234458 A1 | 9/2008 | West |
| 2008/0269420 A1 | 10/2008 | Tong et al. |
| 2009/0036999 A1* | 2/2009 | Egilsson ............... A61F 2/7812 623/36 |
| 2009/0176054 A1 | 7/2009 | Laib et al. |
| 2009/0218307 A1 | 9/2009 | Davies et al. |
| 2009/0233067 A1 | 9/2009 | Doornheim et al. |
| 2009/0240344 A1 | 9/2009 | Colvin et al. |
| 2009/0248168 A1 | 10/2009 | Tuke et al. |
| 2010/0023149 A1 | 1/2010 | Sanders et al. |
| 2010/0161076 A1 | 6/2010 | Pallari |
| 2010/0168439 A1 | 7/2010 | Olson |
| 2010/0191360 A1 | 7/2010 | Napadensky et al. |
| 2010/0249949 A1* | 9/2010 | Bjarnason ............... B32B 37/02 623/36 |
| 2011/0270414 A1 | 11/2011 | Laghi et al. |
| 2011/0285052 A1 | 11/2011 | Wigand et al. |
| 2012/0037263 A1 | 2/2012 | Malloy |
| 2012/0068378 A1 | 3/2012 | Swanson et al. |
| 2012/0091744 A1 | 4/2012 | McKnight et al. |
| 2012/0094060 A1 | 4/2012 | Gershenfeld et al. |
| 2012/0109336 A1* | 5/2012 | Laghi .................. A61F 2/7812 623/33 |
| 2012/0133080 A1 | 5/2012 | Moussa et al. |
| 2012/0137611 A1 | 6/2012 | Oliver |
| 2012/0241993 A1 | 9/2012 | Lipton et al. |
| 2012/0308805 A1 | 12/2012 | Sella |
| 2013/0001834 A1 | 1/2013 | El-Shiblani et al. |
| 2013/0040091 A1 | 2/2013 | Dikovsky et al. |
| 2013/0046394 A1 | 2/2013 | Lipschutz et al. |
| 2013/0073068 A1 | 3/2013 | Napadensky |
| 2013/0078415 A1 | 3/2013 | Rock |
| 2013/0089642 A1 | 4/2013 | Lipson et al. |
| 2013/0246018 A1 | 9/2013 | Spadaccini et al. |
| 2013/0249981 A1 | 9/2013 | Nakagawa et al. |
| 2014/0013962 A1 | 1/2014 | Lipton et al. |
| 2014/0037873 A1 | 2/2014 | Cheung et al. |
| 2014/0050811 A1 | 2/2014 | Lipton et al. |
| 2014/0059734 A1 | 3/2014 | Toronjo |
| 2014/0101816 A1 | 4/2014 | Toronjo |
| 2014/0163445 A1 | 6/2014 | Pallari et al. |
| 2014/0188260 A1 | 7/2014 | Layman et al. |
| 2014/0277585 A1 | 9/2014 | Kelley et al. |
| 2014/0311187 A1 | 10/2014 | Amarasiriwardena et al. |
| 2015/0014881 A1 | 1/2015 | Elsey |
| 2015/0017411 A1 | 1/2015 | Wilkie et al. |
| 2015/0075033 A1 | 3/2015 | Cross et al. |
| 2015/0142150 A1 | 5/2015 | Layman et al. |
| 2015/0174885 A1 | 6/2015 | Khan |
| 2015/0250624 A1 | 9/2015 | Mosler et al. |
| 2015/0321419 A1 | 11/2015 | Linthicum et al. |
| 2015/0321420 A1 | 11/2015 | Karpas et al. |
| 2015/0367375 A1 | 12/2015 | Page |
| 2016/0009029 A1 | 1/2016 | Cohen et al. |
| 2016/0096323 A1 | 4/2016 | Fry et al. |
| 2016/0206448 A1* | 7/2016 | Klutts ................... A61F 5/01 |
| 2016/0228255 A1 | 8/2016 | Samuelson et al. |
| 2016/0297104 A1 | 10/2016 | Guillemette et al. |
| 2016/0324666 A1 | 11/2016 | Barberio |
| 2016/0332382 A1 | 11/2016 | Coward et al. |
| 2017/0027719 A1* | 2/2017 | Bache ................... D04B 1/18 |
| 2017/0036402 A1 | 2/2017 | Zachariasen et al. |
| 2017/0081573 A1 | 3/2017 | Kipke et al. |
| 2017/0105853 A1 | 4/2017 | Jonsson et al. |
| 2017/0173879 A1 | 6/2017 | Myerberg et al. |
| 2017/0190121 A1 | 7/2017 | Aggarwal et al. |
| 2017/0203509 A1 | 7/2017 | Stieghorst et al. |
| 2017/0210064 A1 | 7/2017 | Aw et al. |
| 2017/0216056 A1* | 8/2017 | Hill ..................... A41D 27/06 |
| 2017/0239888 A1 | 8/2017 | Ruiz et al. |
| 2017/0259502 A1 | 9/2017 | Chapiro et al. |
| 2017/0312981 A1 | 11/2017 | Selbertinger et al. |
| 2018/0021140 A1 | 1/2018 | Angelini et al. |
| 2018/0036151 A1* | 2/2018 | Garus .................. A61F 2/7812 |
| 2018/0036952 A1 | 2/2018 | Hocker et al. |
| 2018/0056602 A1 | 3/2018 | Susnjara et al. |
| 2018/0098919 A1 | 4/2018 | Pallari et al. |
| 2018/0153716 A1 | 6/2018 | Martin |
| 2018/0235779 A1 | 8/2018 | Dudding |
| 2018/0236723 A1 | 8/2018 | Susnjara et al. |
| 2018/0281295 A1 | 10/2018 | Tibbits et al. |
| 2018/0281340 A1 | 10/2018 | Brienza et al. |
| 2018/0296343 A1 | 10/2018 | Wei |
| 2018/0353308 A1 | 12/2018 | Tompkins |
| 2018/0368996 A1 | 12/2018 | Van Vliet et al. |
| 2018/0370141 A1 | 12/2018 | Eller et al. |
| 2019/0021880 A1* | 1/2019 | Herr .................... A61F 2/78 |
| 2019/0039309 A1 | 2/2019 | Busbee et al. |
| 2019/0039310 A1 | 2/2019 | Busbee et al. |
| 2019/0053919 A1 | 2/2019 | Egilsson et al. |
| 2019/0070345 A1 | 3/2019 | McBride et al. |
| 2019/0099952 A1 | 4/2019 | Macneish, III et al. |
| 2019/0106593 A1 | 4/2019 | Kenney et al. |
| 2019/0142406 A1 | 5/2019 | Amplatz et al. |
| 2019/0183663 A1 | 6/2019 | Will et al. |
| 2019/0183664 A1* | 6/2019 | Asgeirsson ........... A61F 2/7812 |
| 2020/0016833 A1 | 1/2020 | Yuwaki et al. |
| 2021/0145613 A1 | 5/2021 | Anderson et al. |

FOREIGN PATENT DOCUMENTS

| | | |
|---|---|---|
| CN | 103876263 A | 6/2014 |
| CN | 106003728 A | 10/2016 |
| CN | 107351375 A | 11/2017 |
| CN | 106667629 B | 4/2018 |
| CN | 109414330 A | 3/2019 |
| CN | 110461277 A | 11/2019 |
| DE | 917687 C | 9/1954 |
| DE | 10018987 A1 | 10/2001 |
| DE | 10153796 B4 | 6/2003 |
| DE | 20309318 U1 | 9/2003 |
| DE | 202008015143 U1 | 2/2009 |
| DE | 202009000527 U1 | 3/2009 |
| DE | 102011119591 B3 | 5/2013 |
| DE | 102012009757 A1 | 12/2013 |
| DE | 102013102471 A1 | 9/2014 |
| DE | 102014011373 A1 | 2/2016 |

(56) References Cited

FOREIGN PATENT DOCUMENTS

| | | |
|---|---|---|
| DE | 102014219570 B4 | 5/2016 |
| DE | 102016201002 A1 | 7/2017 |
| DE | 202016001130 U1 | 7/2017 |
| DE | 102016108631 A1 | 11/2017 |
| DE | 202017106997 U1 | 1/2018 |
| DE | 102017106903 B3 | 7/2018 |
| DE | 202019100501 U1 | 3/2019 |
| DE | 102012017324 B4 | 4/2019 |
| DE | 102017126465 A1 | 5/2019 |
| DE | 102018106573 A1 | 9/2019 |
| DE | 102018111442 A1 | 11/2019 |
| DE | 102018124516 A1 | 4/2020 |
| DE | 102018127117 A1 | 4/2020 |
| DE | 102012022484 B4 | 6/2020 |
| DE | 102018131550 A1 | 6/2020 |
| DE | 102018133486 A1 | 6/2020 |
| EP | 1274559 B1 | 1/2003 |
| EP | 0876130 B1 | 3/2006 |
| EP | 1854621 B1 | 11/2007 |
| EP | 2090273 A2 | 8/2009 |
| EP | 2568935 A2 | 3/2013 |
| EP | 2599464 A1 | 6/2013 |
| EP | 3100704 A1 | 12/2016 |
| EP | 2599464 B1 | 1/2017 |
| EP | 3156216 A1 | 4/2017 |
| EP | 3243632 A1 | 11/2017 |
| EP | 3300700 A3 | 7/2018 |
| EP | 3454792 A1 | 3/2019 |
| FR | 1243060 A | 10/1960 |
| FR | 1331581 A | 7/1963 |
| FR | 2095097 A5 | 2/1972 |
| FR | 2479923 A1 | 10/1981 |
| FR | 2583334 A1 | 12/1986 |
| FR | 2956590 B1 | 8/2011 |
| GB | 2455167 A | 6/2009 |
| JP | H0742024 A | 2/1995 |
| JP | 2003533367 A | 11/2003 |
| WO | 0069747 A1 | 11/2000 |
| WO | 0178968 A1 | 10/2001 |
| WO | 03016067 A2 | 2/2003 |
| WO | 03051241 A1 | 6/2003 |
| WO | 2006113585 A2 | 10/2006 |
| WO | 2006135851 A2 | 12/2006 |
| WO | 2013072064 A1 | 5/2013 |
| WO | 2013121230 A1 | 8/2013 |
| WO | 2013142343 A1 | 9/2013 |
| WO | 2014025089 A1 | 2/2014 |
| WO | 2014130878 A1 | 8/2014 |
| WO | 2014144985 A1 | 9/2014 |
| WO | 2015017421 A2 | 2/2015 |
| WO | 2015059502 A1 | 4/2015 |
| WO | 2015084422 A1 | 6/2015 |
| WO | 2015139095 A1 | 9/2015 |
| WO | 2015197495 A1 | 12/2015 |
| WO | 2016033469 A1 | 3/2016 |
| WO | 2016057853 A1 | 4/2016 |
| WO | 2017011753 A1 | 1/2017 |
| WO | 2017012888 A1 | 1/2017 |
| WO | 2017019681 A1 | 2/2017 |
| WO | 2017062690 A1 | 4/2017 |
| WO | 2017079475 A1 | 5/2017 |
| WO | 2017081040 A1 | 5/2017 |
| WO | 2017136405 A1 | 8/2017 |
| WO | 2017194479 A1 | 11/2017 |
| WO | 2018044759 A1 | 3/2018 |
| WO | 2018054966 A1 | 3/2018 |
| WO | 2018088965 A1 | 5/2018 |
| WO | 2018151923 A1 | 8/2018 |
| WO | 2018183803 A1 | 10/2018 |
| WO | 2018187514 A1 | 10/2018 |
| WO | 2019091716 A1 | 5/2019 |
| WO | 2019110170 A1 | 6/2019 |
| WO | 2019179894 A1 | 9/2019 |
| WO | 2019219514 A1 | 11/2019 |
| WO | 2020069817 A1 | 4/2020 |
| WO | 2020074374 A1 | 4/2020 |
| WO | 2020120187 A1 | 6/2020 |
| WO | 2020126501 A1 | 6/2020 |
| WO | 2021101806 A1 | 5/2021 |

OTHER PUBLICATIONS

Franzino, "3 Ways to Adhere Silicone to Silicone," Albright Technologies Monthly Insider, Issue 17, Mar. 2013, 2 Pages.

"CF19-2186; Medium Cure Rate, General Purpose Silicone Elastomer," NuSil, May 21, 2014, retrieved from https://nusil.com/en/product/CF19-2186_medium-cure-rate-general-purpose-silicone-elastomer?h=cf19 on Jan. 3, 2020.

"MED-4950; Liquid Silicone Rubber," NuSil, May 16, 2014, retrieved from https://nusil.com/en/product/MED-4950_liquid-silicone-rubber?h=med-4950 on Jan. 3, 2020, 3 Pages.

Ventola, "Medical Applications for 3D Printing: Current and Projected Uses," P&T, vol. 39, No. 10, Oct. 2014, pp. 704-712.

Femmer et al., "Print Your Own Membrane: Direct Rapid Prototyping of Polydimethylsiloxane," Royal Society of Chemistry, vol. 14, 2014, pp. 2610-2613.

"A True Rotary 3D Printer?" element14, Jun. 27, 2015, retrieved from www.element14.com/community/thread/25031a-true-rotary-3, Oct. 22, 2018.

Ostermeier, "3D Printing With Silicone," Assembly Magazine, Oct. 2, 2015, pp. 1-4.

Coulter et al., "4D Printing Inflatable Silicone Structures," 3D Printing and Additive Manufacturing, vol. 2, No. 3, 2015, pp. 1-6.

Cagle, "A Computational Tool to Enhance Clinical Selection of Prosthetic Liners for People with Lower Limb imputation," University of Washington, 2016, pp. 1-154.

Hoy, "Design and Implementation of a Three-Dimensional Printer Using a Cylindrical Printing Process," Electrical Engineering Department, California Polytechnic State University, 2016, pp. 1-31.

Momeni et al., "A Review of 4D Printing," Materials and Design, vol. 122, Mar. 1, 2017, pp. 42-79.

O'Bryan et al., "Self-Assembled Micro-Organogels for 3D Printing Silicone Structures," Science Advances, vol. 3, May 10, 2017, pp. 1-8.

Rios, "Evaluation of Advanced Polymers for Additive Manufacturing," Oak Ridge National Laboratory, Sep. 8, 2017, pp. 1-22.

"Rethinking Foam-Carbon's Lattice Innovation," retrieved from www.carbon3d.com, Dec. 6, 2017, pp. 1-9.

Kiessling et al., "Gravity-Drawn Silicone Filaments: Production, Characterization, and Wormlike Chain Dynamics," American Chemical Society, Applied Materials & Interfaces, vol. 9, 2017, pp. 39916-39920.

Low et al., "Perspective on 3D Printing of Separation Membranes and Comparison to Related Unconventional Fabrication Techniques," Journal of Membrane Science, 2017, pp. 596-613.

Tian et al., "Silicone Foam Additive Manufacturing by Liquid Rope Coiling," Science Direct, 2017, pp. 196-201.

Dhokia et al., "The Design and Manufacture of a Prototype Personalized Liner for Lower Limb Amputees," Science Direct, 2017, pp. 476-481.

Jasiuk et al., "An Overview on Additive Manufacturing of Polymers," The Minerals, Metal & Materials Society, vol. 70, No 3, Jan. 25, 2018, pp. 275-283.

Woodford, "Centrifuges," Jun. 24, 2018, retrieved from www.explainthatstuff.com/cenliiruges on Nov. 7, 2018, pp. 1-10.

"How Liners Work," Ottobock, retrieved from www.ottobockus.com/prosthetics on Oct. 22, 2018, 1 Page.

"Technology: The Process in a Nutshell," Spectroplast AG, retrieved from www.spectroplast.com/technology on Oct. 31, 2018, pp. 1-5.

Liravi et al., "A Hybrid Additive Manufacturing Method for the Fabrication of Silicone Bio-Structures: 3D Printing Optimization and Surface Characterization," Elsevier: Materials and Design, 2018, pp. 46-61.

Ruiz et al., "3D Printing Assisted Method of Manufacturing a Perforated Silicone Prosthetic Limb Liner," RESNA Annual Conference, 2017, pp. 1-4.

(56) References Cited

OTHER PUBLICATIONS

Zhakeyev et al., "Additive Manufacturing: Unlocking the Evolution of Energy Materials," Advanced Science, vol. 4 2017, pp. 1-44.
Javaid et al., "Current Status and Challenges of Additive Manufacturing in Orthopaedics: An Overview," Journal of Clinical Orthopaedics and Trauma, 2019. pp. 380-386.
McColl et al., "Design and Fabrication of Melt Electrowritten Tubes Using Intuitive Software," Materials and Design , 2018, pp. 46-58.
"3D Printing of Silicone Parts in Additive Manufacturing," Capri Systec Ltd, May 22, 2018, pp. 1-3.
Li et al., "Review of 3D Printable Hydrogels and Constructs," Materials and Design, Issue 159, 2018, pp. 20-38.
Helmenstine, "What Is Centripetal Force? Definition and Equations," Thought Co., Sep. 21, 2018, pp. 1-3.
Liravi et al., "Additive Manufacturing of Silicone Structures: A Review and Prospective," Additive Manufacturing, Issue 24, 2018, pp. 232-242.
"3D Printing With Silicones—A Breakthrough in Additive Manufacturing," retrieved from www.plastics.gl/3d-printing-2/3d-printing-with-silicones-a-breakthrough-in-additive-manufacturing/ on Oct. 31, 2018.
Culmone et al., "Additive Manufacturing of Medical Instruments: A State-of-the-Art Review," Additive Manufacturing, Issue 27, 2019, pp. 461-473.
OOI, "How to 3D Print Rubber-Like Materials," All3DP, retrieved from https://all3dp.com/2/how-to-3d-print-rubber-like-materials/ on Aug. 13, 2019, pp. 1-7.
"Progressive Cavity Pumps—Volumetric Dosing Systems," retrieved from www.viscotec.de/en/technology/ retrieved on Aug. 13, 2019.
Yuan et al., "Polymeric Composites for Powder-Based Additive Manufacturing: Materials and Applications," Progress in Polymer Science, vol. 91, 2019, pp. 141-168.
Chen et al., "3D Printed Multifunctional, Hyperelastic Silicone Rubber Foam," Advanced Functional Materials, vol. 29, Issue 1900469, 2019, pp. 1-9.
"About the Silicone Molding Design Manual," Albright Technologies 6th Edition, pp. 1-248.
Porter et al., "Additive Manufacturing Utilizing Stock Ultraviolet Curable Silicone," Solid Freeform Fabrication 2017: Proceedings of the 28th Annual International Solid Freeform Fabrication Symposium, pp. 1-13.
Liravi et al., "A Hybrid Method for Additive Manufacturing of Silicone Structures," Solid Freeform Fabrication 2017: Proceedings of the 28th Annual International Solid Freeform Fabrication Symposium, pp. 1-21.
Toursangsaraki, "A Review of Multi-Material and Composite Parts Production by Modified Additive Manufacturing Methods", Jun. 12, 2018, pp. 1-25.
Unkovskiy et al., "Direct 3D Printing of Silicone Facial Prostheses: A Preliminary Experience in Digital Workflow," The Journal of Prosthetic Dentistry, Aug. 2018, pp. 1-6.
Coulter et al., "Production Techniques for 3D Printed Inflatable Elastomer Structures. Part 1—Fabricating Air-Permeable Forms and Coating with Inflatable Silicone Membranes via Spray Disposition", Mar. 2018, pp. 1-17.
Duoss et al., "Three-Dimensional Printing of Elastomeric, Cellular Architectures with Negative Stiffness," Advanced Functional Materials, vol. 24, 2014, pp. 4905-4913.
"MED-4901; Liquid Silicone Rubber," NuSil, Nov. 2018, retrieved from https://nusil.com/product/med-4901_liquid-silicone-rubber on Nov. 11, 2019, 3 Pages.
"MED-6345; Soft Silicone Adhesive," NuSil, Nov. 2018, retrieved from https://nusil.com/en/product/MED-6345_soft-silicone-adhesive?h=MED-6345 on Nov. 11, 2019, 3 Pages.
International Search Report from PCT Application No. PCT/US2019/060863, dated Apr. 15, 2020.
International Search Report from PCT Application No. PCT/US2019/060881, dated Apr. 20, 2020.
Hsu, L.H.: "The development of a rapid prototyping prosthetic socket coated with a resin layer for transtibial amputees", Prosthetics and Orthotics International, vol. 34, No. 1, Mar. 1, 2010 (Mar. 1, 2010), pp. 37-45.
Nicholas Herbert et al, "A preliminary investigation into the development of 3-D printing of prosthetic sockets", Journal of Rehabilitation Research and Development, vol. 42, No. 2, Jan. 1, 2005 (Jan. 1, 2005), US, pp. 141.

* cited by examiner

FIG. 2G
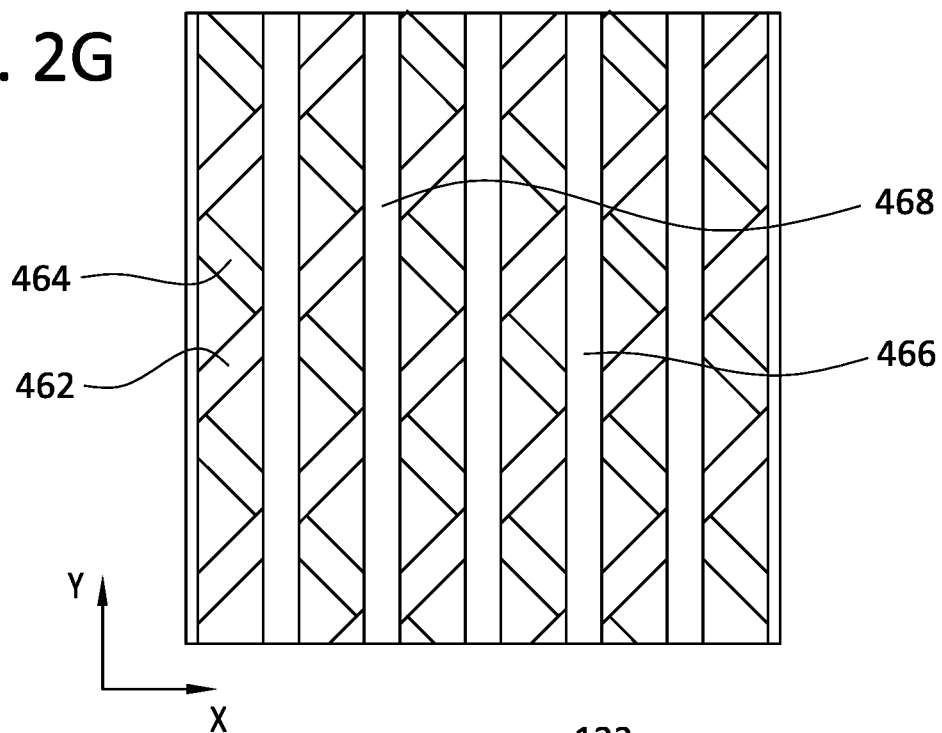
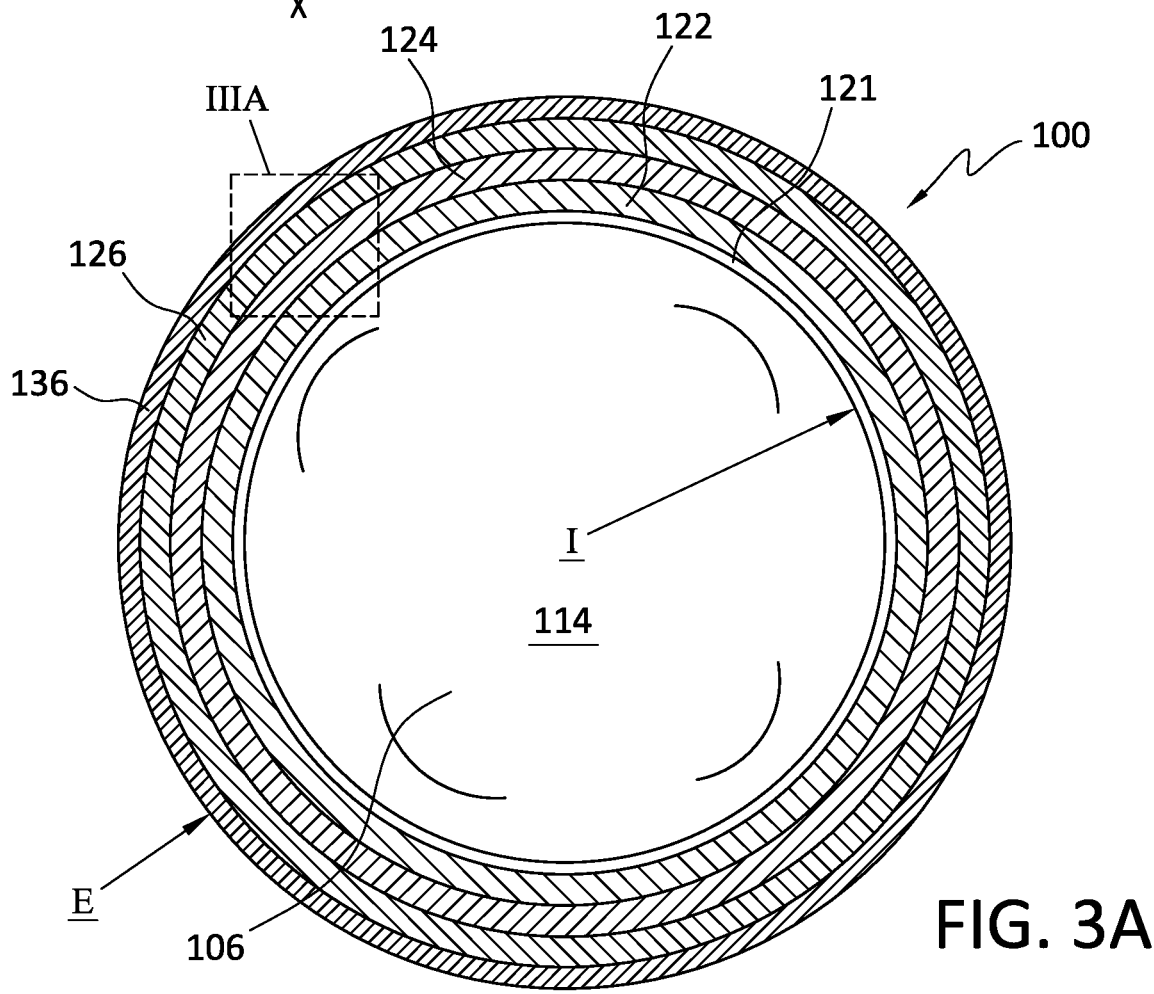
FIG. 3A

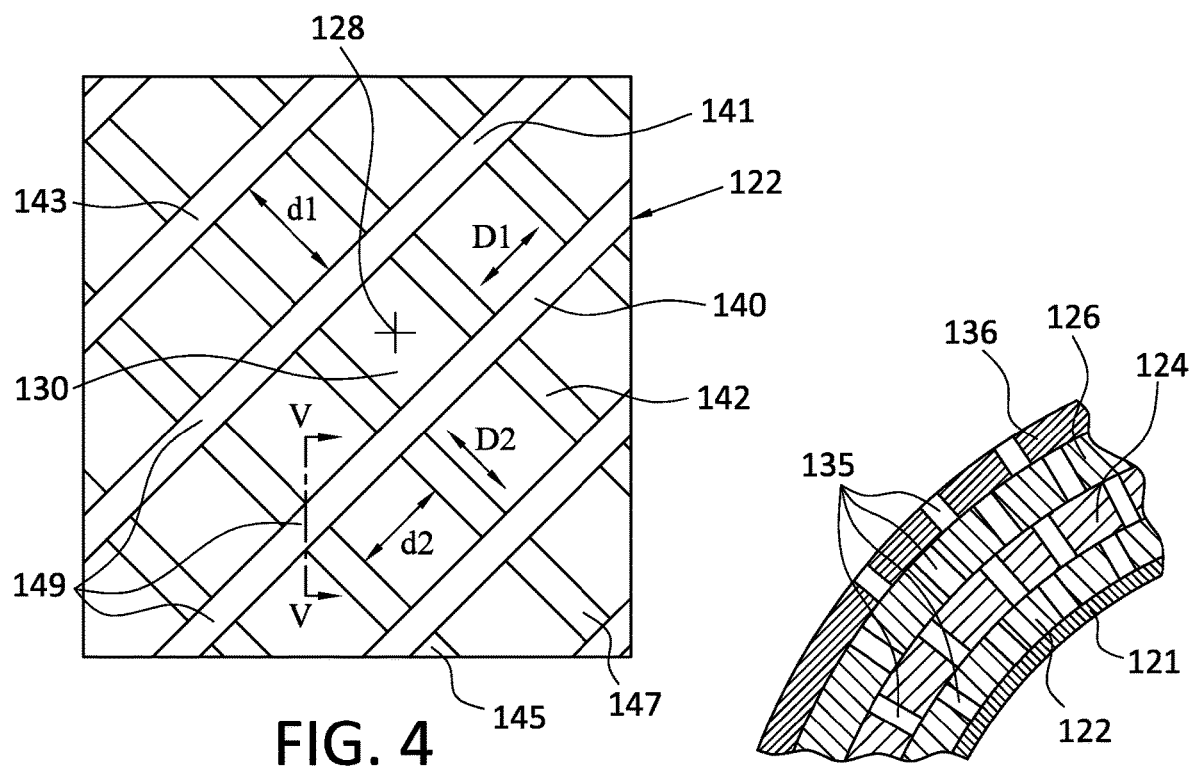
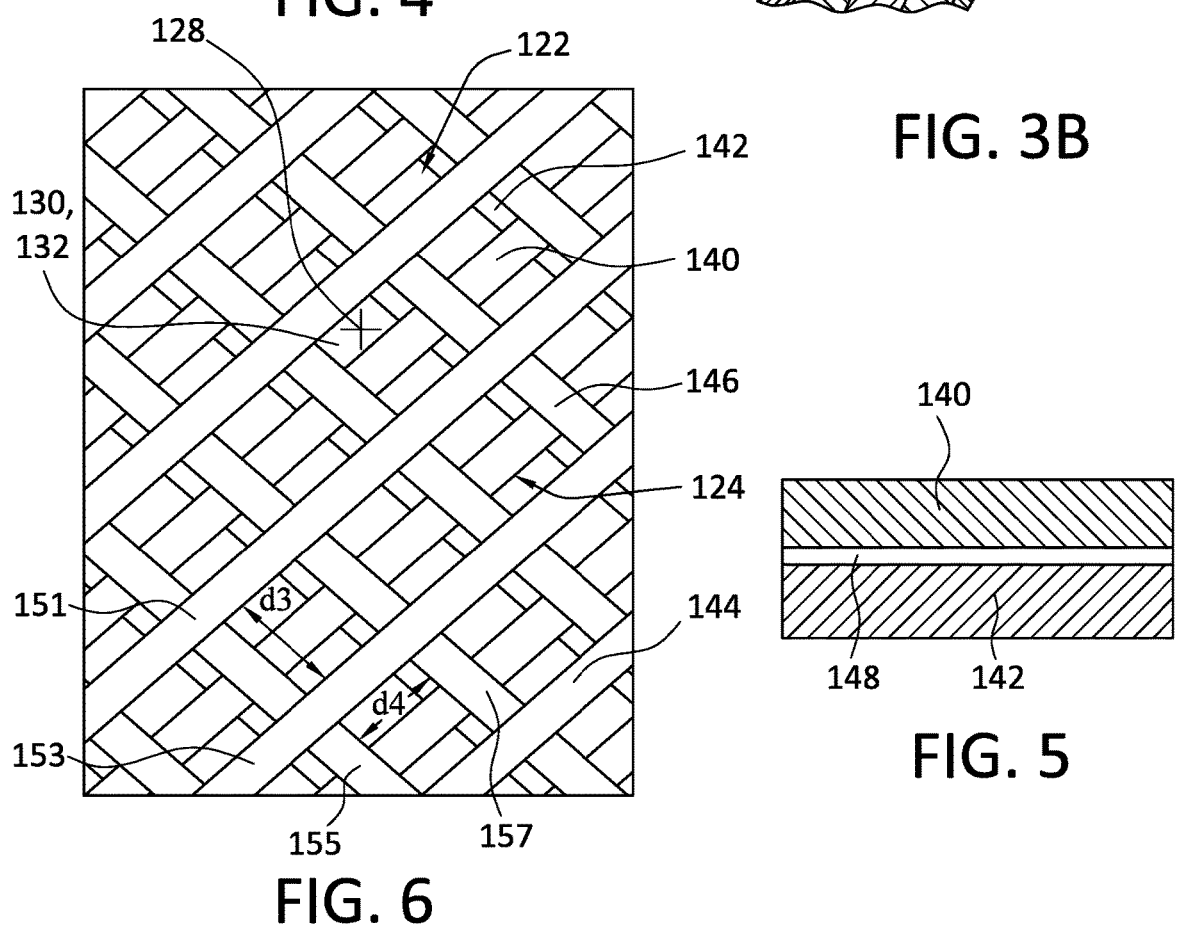
FIG. 4
FIG. 3B
FIG. 6
FIG. 5

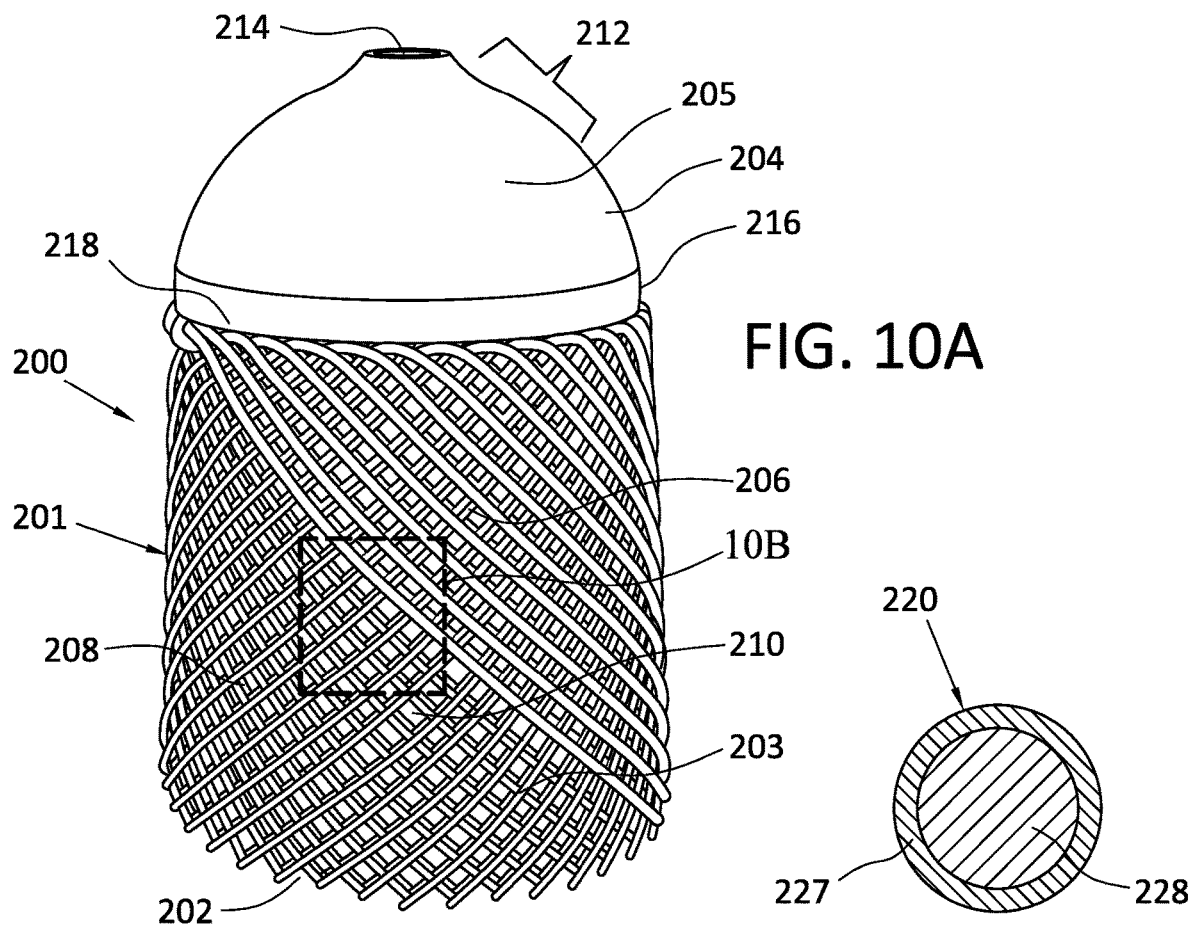
FIG. 10A
FIG. 10C
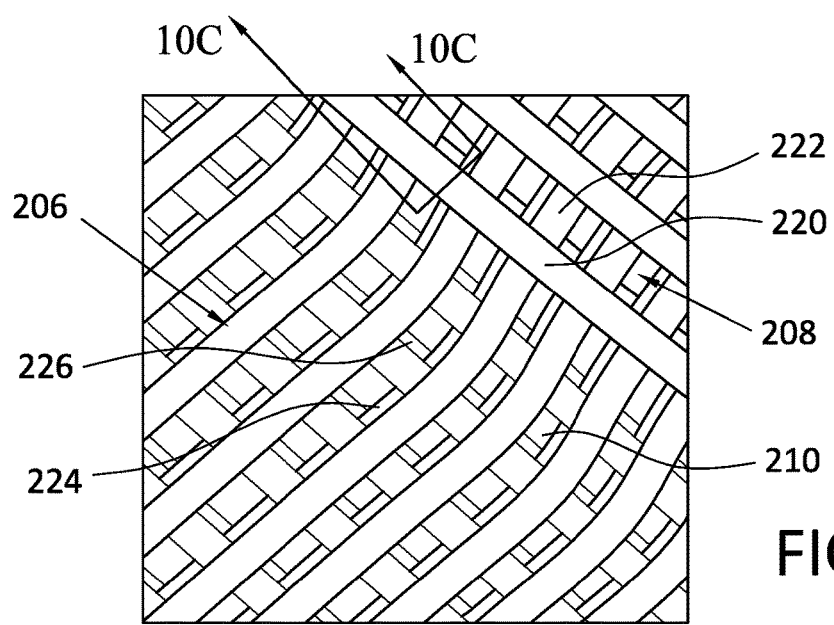
FIG. 10B

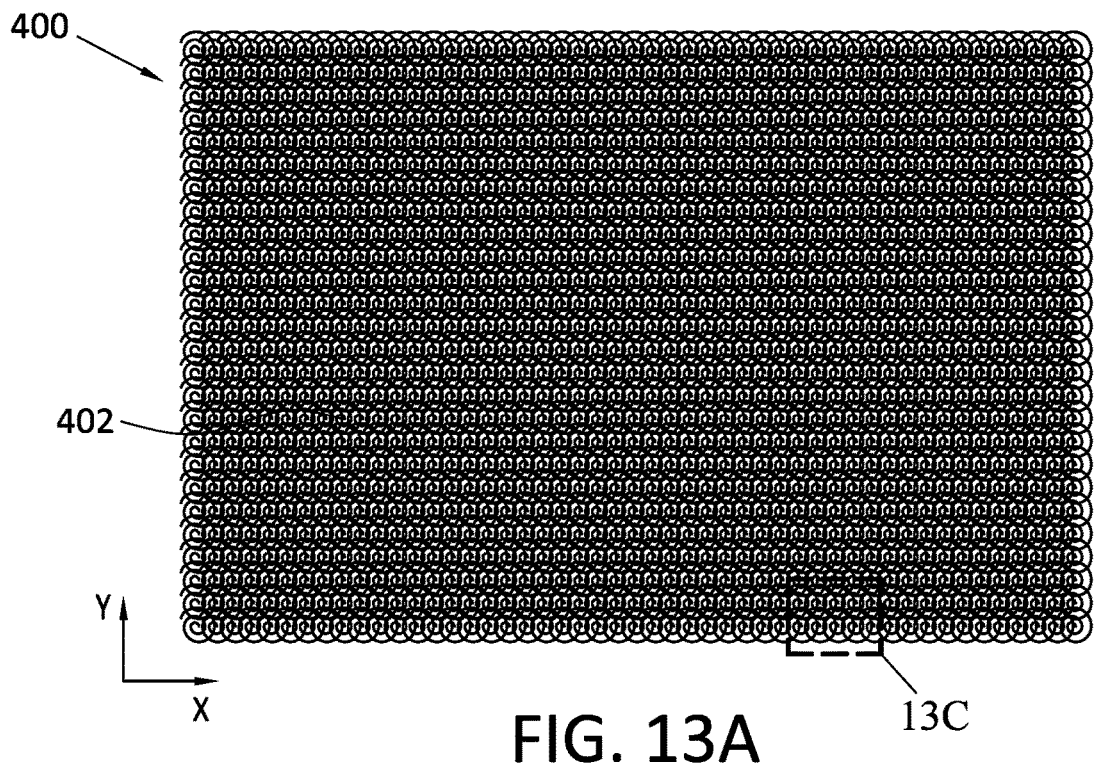
FIG. 13A
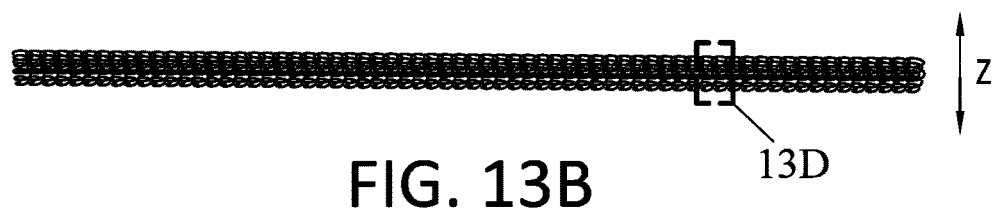
FIG. 13B
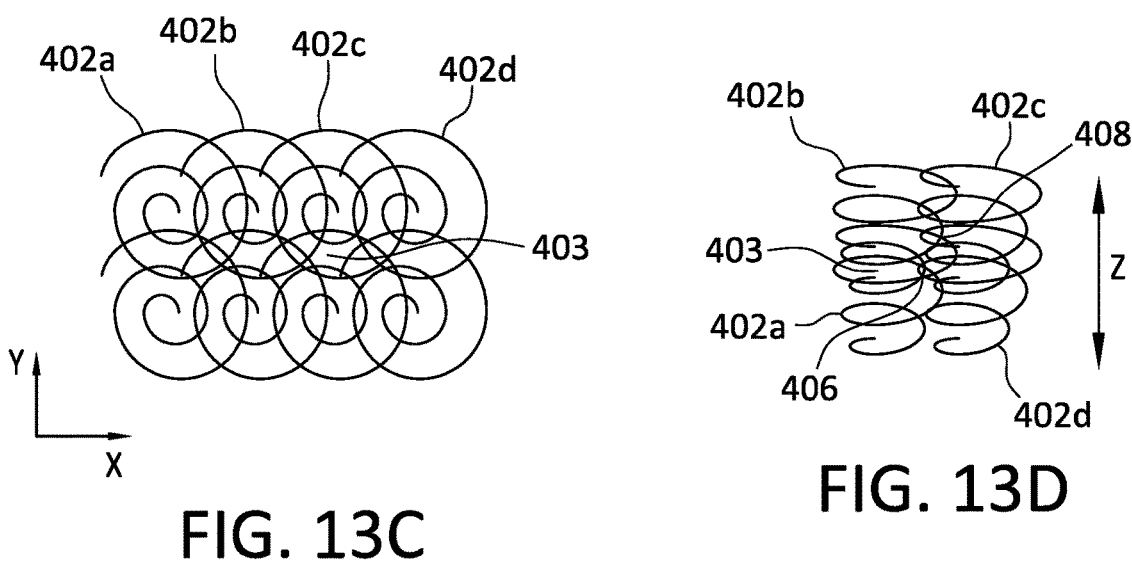
FIG. 13C
FIG. 13D

MEDICAL DEVICE INCLUDING A STRUCTURE BASED ON FILAMENTS

CROSS-REFERENCE TO RELATED APPLICATIONS

This application incorporates by reference U.S. application no. [ ] entitled "ADDITIVE MANUFACTURING SYSTEM, METHOD AND CORRESPONDING COMPONENTS FOR ELASTOMERIC MATERIALS," by the certain inventors of this disclosure and filed on Nov. 12, 2019. This application also incorporates by reference U.S. provisional application No. 62/759,237, filed on Nov. 12, 2018, and 62/760,030, filed on Nov. 12, 2018.

FIELD OF THE ART

The disclosure relates to medical devices, such as prosthetic or orthopedic devices, and an exemplary embodiment is a liner, sleeve, or sock, generally referred to herein as a "liner," for suspension and comfort in a prosthetic device system. The exemplary embodiments are formed from a lattice cellular or solid structure defined by a plurality of discretely formed filaments.

BACKGROUND

Liners in prosthetic uses are widely known and are used as an interface between a residual limb and a prosthetic socket, allowing a user to comfortably and safely wear the prosthetic socket and prostheses attached thereto, such as prosthetic limbs. Liners may, for instance, provide cushioning between the end of the residual limb and the prosthetic socket, protecting the limb from developing pressure points as a user's weight is applied to the hard components of the prosthetic socket during use. Liners may additionally provide for improved pressure distribution along the residual limb and within the prosthetic socket. In vacuum suspension-type prosthetic systems, a liner may also protect the residual limb from being exposed to an elevated vacuum for extended periods of time.

Polymeric, particularly elastomeric, materials are commonly used for constructing liners. For example, a medical-grade silicone may be used that is naturally compatible with human tissue and resistant to fluids and bacteria, reducing the risk of infection. These liners, despite limitations on breathability, often are designed to remain fresh and odor-free after each use, and have lasting strength and thickness despite repeated use. But many liners may not achieve such desired results upon repeated use, depending on the characteristics of the user.

An elastomeric material may be preferred, although not limited, for constructing the liner because it has inherent elasticity that conforms to a residual limb. The elasticity of the liner may be tailored to inhibit elasticity in different directions, such as axially, but enhanced in one direction (radially) relative to another direction such (axially).

Normally a liner is constructed by molding the elastomeric material between male and female molds to form a solid layer of elastomeric material that may closely encapsulate the residual limb. The elastomeric material may be extruded into a predetermined shape. Either in molding or extrusion, the liner is created as having a fixed cross-section profile, without control for adapting the molded or extruded part profile.

This fixed cross-section profile is generally a solid mass of elastomeric material that is both vapor-and-liquid impermeable, and the solid layer is formed cohesively as an entirely monolithic body. To provide sufficient cushioning and protection of the residual limb, such liners typically comprise a relatively thick layer of fluid-impermeable elastomeric material. The thickness may be increased at a distal end of the liner to provide additional cushioning at the point of the liner where the weight of the user is most pronounced against the prosthetic socket.

Because the liner is constructed from a unitary wall or solid layer of elastomeric material, usually formed or cured from a liquid resin poured into the molds or extruded into shape, the material may have uniform properties throughout the body of the liner, or simplified properties among various components to the liner (e.g. a taper in thickness). An example of a method for manufacturing a liner is found in U.S. Pat. No. 6,626,952, issued on Sep. 30, 2003, and an example of a liner having multiple components and/or properties is found in U.S. Pat. No. 6,136,039, issued on Oct. 24, 2000, each of which is incorporated herein by reference.

A common practice is to attach a textile material to an exterior surface of the liner, the textile material having defined properties that may provide customized or desired features at specific locations. The solid elastomeric layer may be cured against the textile material, which requires pre-processing steps, such as sewing and shaping, to have desired properties. One example of the time-consuming and cost-increasing pre-processing steps is the stitching of a distal seam in a textile tube to shape the textile tube into a liner shape. Other components may be provided in a liner, such as a hard distal end cap.

Stitching and securing a textile to a liner body of an elastomeric material, and additional components of a liner may cause pressure points when the liner is worn by a user and pressed against a hard socket. Efforts have been made to minimize such effects, as in U.S. Pat. No. 9,770,891, issued on Sep. 26, 2017, which is incorporated herein by reference. But attention is still desired for simplifying processes used to provide such textile or other components to a liner body and by yet further minimizing pressure points.

A known problem in liners is the buildup of moisture and heat between the residual limb and the liner, which can lead to discomfort, unpleasant odors, "milking," "pistoning," and breakdown of tissue. For example, medical-grade silicone is hydrophobic because it is vapor- and liquid-impermeable. Sweat may build-up between the residual limb and the liner, which may cause slippage of the liner from the residual limb and discomfort. This may lead to the risk of non-compliant use of the prosthetic system or even of catastrophic failure of the prosthetic system during use.

There is a balance between providing a liner having sufficient cushioning and thickness to protect the residual limb from harmful extended contact with hard or rigid surfaces and providing a liner that is breathable to mitigate heat and moisture buildup. A concern arises in whether the liner can maintain the same strength, thickness, compression, and general functionality in a liner having a ventilated structure as in a conventional solid-walled liner. There is likewise a desire to maintain the liner as constructed from an approved and accepted medical-grade elastomeric material, such as silicone.

Efforts to bridge this gap have included providing wicking layers or absorbent materials within the silicone layer or between the silicone layer and the textile material, which steps may increase the cost and complexity of constructing a liner. An example of such efforts is found in U.S. Pat. No. 9,629,732, granted on Apr. 25, 2017, and incorporated herein by reference. Efforts to provide apertures, or wicking layers and absorbent materials may impair the functionality of a liner or result in a liner having inferior mechanical properties relative to a conventional solid-walled liner. Such past ventilated liners may prevent or preclude other desirable features in liners, such as external surface peripheral profiles, as in U.S. Pat. No. 7,118,602, issued on Oct. 10, 2006, and seal systems as in U.S. Pat. No. 9,066,821, issued on Jun. 30, 2015, each reference being incorporated herein by reference.

There still exists a need for a liner that achieves the structural and cushioning benefits of solid-walled, conventional liners but which can mitigate the buildup of heat and moisture, while preserving its construction from a medical-grade material and accommodating various features common in conventional liners.

Another problem in existing systems and methods for producing liners is the difficulty and cost of providing a custom-fitted prosthetic system with features that correspond to the needs at different portions of the residual limb. Each residual limb has unique dimensions and shape, and the efforts of a trained prosthetist must assess a user's needs should the user's needs be outside normal shapes and sizes of liners. Individuals may have different bony mass structure and soft-tissue, depending on how the residual limb occurred, and it is difficult to meet the unique limb shape and needs of the individual residual limb, particularly as, due to swelling or weight change, the dimensions and needs of a particular user may be dynamic and change.

As it is difficult to achieve the structural and functional needs of each residual limb, it is desirable to provide a liner that can meet the demands of each user, whether the liner is for lower or upper extremities, and whether the user requires elevated vacuum, seal-in expulsion, and locking suspension systems. Custom liners may be provided for amputees of all lifestyles and activity levels, and there is difficulty meeting the demands of all such individuals with standard conventional-sized liners. Individuals may require material additives for easier donning and doffing, and skin-treatment additives, and desire conventional liner features in a custom-fitted liner.

Because many medical devices having elastomeric materials such as medical-grade silicone are formed by injection molding, where a silicone resin is injected into a space defined by a negative mold of the medical device, most medical devices do not have a desired degree of customized properties based on the functionality of different regions of a user's body but have uniform properties throughout. In the example of a liner, however, it may be desired to have more elasticity at and behind the knee compared to above, below, and to the sides of the need, or a different degree of breathability may be desired at regions proximate active muscle groups that generate more heat and fluid. There is a need for a medical device that provides custom properties at desired locations around the medical device rather than uniform properties.

There is a need for a liner that can be tailored to the demands of an individual user while offering accommodation for conventional liner features. More generally, there is a need for medical devices constructed from elastomeric materials that offer a desirable balance of breathability and mechanical properties to withstand an ordinary daily use of the device.

SUMMARY

The balance of strength, comfort, breathability, and other desired properties of elastomeric and other polymer-based, preferably elastomer-based medical-grade materials in medical devices such as prosthetic and orthopedic devices, is addressed in embodiments of the disclosure. These embodiments exemplify a liner comprising discretely and continuously deposited layers based on filaments of a polymeric material, such as silicone or other elastomers, used in conventional liners while maintaining at least equivalent mechanical strength and other mechanical properties of such conventional liners. While such liners may be constructed from the same medical-grade elastomeric material and possess the same mechanical and chemical properties of conventional liners, the lattice structure of the embodiments provides improved cushioning, moisture removal, and/or breathability over known conventional liners.

The embodiments may be provided in combination with textile covers, reinforcement layers, material additives, and other desired features in conventional liners while having the improved features. While medical-grade elastomeric material is discussed, it will be understood that the disclosure is by no means limited to medical-grade material and may make use of any suitable material.

The exemplary embodiments possess characteristics that can be extended to a wide range of medical devices including prosthetic or orthopedic parts, medical implants, medical tubing, prostheses, and other parts or devices. The characteristics may be adapted according to desired properties or needs and customized to address the needs of users. For example, the characteristics of the embodiments can be used in devices made by known medical-grade elastomeric materials, thereby removing the necessity for material approval and streamlining regulatory acceptance.

Exemplary liner embodiments are arranged to effectively manage perspiration formed by a limb, prevent slippage of the liner on the limb, and provide suitable cushioning for a limb. The exemplary embodiments described are discussed and shown within the context of a liner in a prosthetic system for use with a hard socket. However, the disclosure is not limited to such a prosthetic embodiment or the exact uses described and embraces any use requiring perspiration management, prevention of slippage, cushioning of the limb, or any other structural and/or functional benefit that may derive in whole or in part from the principles of the disclosure. Principles described herein may be extended to any prosthetic, orthopedic, or medical device, and are in no manner merely limited to liners.

In an exemplary embodiment, a liner advantageously bridges the gap between the strength of a solid-layer wall liner and the need for breathability while using a medical-grade material. The liner may be customized to have features at particular locations corresponding to the needs of individual users, minimizing cost and complexity of manufacturing, and offering physical structure and functionality that benefit different requirements. The liner is just an example of the different structures that can be manufactured and configured according to principles described herein.

According to the exemplary embodiment, the liner has a first or proximal end, a second or distal end, and a tubular liner body defined between the first and second ends. The liner body preferably comprises a base layer formed from an elastomeric material, such as silicone, and having an inner surface extending along with an interior of the tubular liner and defining a periphery thereof. The base layer defines a plurality of openings extending preferably through a thickness thereof. As the base layer should secure against the skin of a user about the residual limb, the base layer may have more combined solid surface area than a combined area of the plurality of openings to provide an effective skin interface. The inner surface of the base layer is preferably smooth because it has a generally uniform surface elevation aside from the openings.

The base layer may comprise a plurality of filaments integrally adjacent to and/or chemically bonded to one another to form a continuous solid layer. The filaments are aligned along one another and are chemically bonded to along their length to an adjacent filament without a gap or interruption. Such structure can be formed to constitute a film that is both vapor and liquid impermeable. One filament may be continuously formed against an adjacent filament, whereas the adjacent filament may be formed with gaps along its length, with yet another filament on an opposing side of the adjacent filament to form an apertured or ventilated layer; however such apertured or ventilated layer has apertures positively formed without mechanically or chemically perforating a solid layer to form such apertures, offering control in shape and size of such apertures. A solid or continuous film or layer may be formed, and then material may be removed in any suitable manner to define the apertures.

A first layer formed from an elastomeric material is secured to an outer surface of the base layer (so the base layer is secured to the inner side of the first layer) and comprises a first set of interstices having axes corresponding to axes of the openings of the base layer. The first layer comprises a first sub-layer including a plurality of first filaments arranged in a first direction and a second sub-layer including a plurality of second filaments arranged in a second direction. The second sub-layer overlaps the first sub-layer and forms the plurality of interstices therebetween. The material properties of an elastomeric material forming the base layer may differ from material properties of an elastomeric material forming the first layer, such as having a different durometer, such as a skin-friendly durometer. The base layer may include a skincare additive such as a moisturizer, an antimicrobial composition, aloe vera, or otherwise, whereas the first layer may not, and vice versa.

Each filament may have a uniform cross-section extending along its length in a predetermined shape. Each filament is formed discretely and extends continuously relative to adjacent filaments. These discretely formed filaments may constitute basic building blocks of the liner or medical device structure. While the preferred embodiments display the filaments as arranged in a lattice-like network to form a lattice structure, they may be arranged relative to one another at varying distances and orientations relative to one another. The filaments may be arranged relative to one another in an infinite number of coordinates relative to one another in X-, Y-, Z-planes and/or coordinates. A cross-section of the filaments may be modified to resemble any desired geometric shape such as a square, rectangle, triangle, or circle, while an exemplary shape is a generally round configuration. The cross-section may be asymmetric and be different at various lengths or locations of a continuous filament.

The first and second sub-layers of the first layer are preferably chemically bonded to one another, and might be formed from the same elastomeric material but are compatible materials nonetheless to assure bonding. Likewise, the base layer and the first sub-layer are chemically bonded to one another from compatible materials. In this manner, the sub-layers integrally form an inseparable structure and continuous structure bonded together to act mechanically as a monolithic structure. By chemically bonding, a preferred embodiment is without an adhesive, in that the filaments are bonded together as the elastomeric material defining the filaments is a curing material and sufficiently fluid for the layers to at least slightly blend at an interface, however it is not outside the scope of the disclosure to use an adhesive, a primer, or any other suitable means.

Additional layers may be secured to a second or outer side of the first layer (i.e., a second layer formed similarly to the first layer and secured to the first layer). These additional layers are likewise preferably formed together as an inseparable and continuous structure to act mechanically as a monolithic structure. The second layer may be chemically bonded to the second sub-layer of the first layer and comprise a plurality of interstices that have axes corresponding to the interstices of the first layer.

A textile or fabric layer may be secured to the outer periphery of the first layer or the additional layers, and may be breathable to permit passage of air from the inner surface of the base layer through an entire thickness of the first layer and additional layers, so an axis extends through each interstice of the first layer and the corresponding interstice of an additional layer, and a respective or corresponding opening of the base layer. The breathability is not limited to merely passing through a wall thickness, but air may transfer in all directions within the lattice network of interstices which define the lattice structure. At least one layer of filaments may be arranged, such as by size or material properties, to impregnate at least part of the textile layer.

The openings of the base layer and the interstices of the first layer and additional layers are arranged in a predetermined shape and pattern in a controlled manner to form a lattice structure. While materials of the base, first, and additional layers may be elastomeric, they may be formed of the same material or of different materials. The base, first, and additional layers may have different or similar mechanical properties. Regarding the mechanical properties, the layers may be tailored to different mechanical properties according to the location of the layer relative to the liner. For example, the base layer may have a lower durometer as a whole than the first layer. A region corresponding to a joint such as a knee may be formed from materials imparting greater elasticity or breathability than an adjacent region.

The materials are preferably compatible materials to allow for chemical bonding, so they permanently are joined to each other and may share at least a blended region in which the materials of the layers intermix or interlock to form the permanent chemical bond. Other features, such as seals, volume control pads, cushioning pads, distal caps, etc. may be formed from compatible materials and chemically bonded to or within a thickness of the liner body. Intermediate layers may be provided among layers to improve adhesion among layers, textiles, or other elements chemically bonded or mechanically interlock.

By arranging discretely deposited filaments and layers of materials having different properties, the liner advantageously provides enhanced precision in attaining desired mechanical properties, structures, and functions over existing liners. Inner layers may provide greater comfort through having a lower durometer, for example, while outer layers may have a greater thickness and greater elasticity to provide mechanical strength and desired functional properties. In some embodiments, the discretely deposited layers of material may comprise multi-layer depositions, points, or filaments of different materials having different properties.

According to a variation, the filaments may be arranged with co-extruded materials, so two materials are co-axial, with an outer layer formed from a material having a different hardness (or other property) than a material forming the inner layer. Among some reasons, the outer layer can protect a soft inner layer and form strong chemical bonds with adjacent filaments. In other variations, the elastomeric material may be co-extruded with textiles such as yarn. In other embodiments, the elastomeric material may be extruded as a continuous filament with different properties at different locations provided by in-line dosing of additives, for example the addition of oil at certain locations to achieve a lower durometer. The filaments may be hollow to allow for using higher durometer, higher durability materials while maintaining cushioning associated with lower durometer materials. The stretchability of the inner layer can be controlled by the outer layer while permitting compressibility of the soft inner layer. This allows the discretely formed filaments to have the advantage of providing multiple types of materials simultaneously. For example, the liner can have properties and advantages of a hard, durable material and the properties and advantages of a soft cushioning material.

The combination or bonding of adjacent filaments can be extended to solid wall portions of the liner that are vapor- and liquid-impermeable solid-walled liners, or other medical devices having solid wall portions or which are solid entirely. Preferably, the solid wall portions may be formed from a plurality of adjacent and abutting filaments also discrete and continuous. The resultant structure is preferably smooth and continuous in the sense there is no identification of each filament of the plurality of discrete filaments due to their direct adjacent proximity, whether mechanical, tactile, or functional. The resultant structure of the adjacent filaments is other filaments having blended chemical bonding by adjacent and abutting filaments in X-, Y-, Z-planes and/or coordinates.

A plurality of filaments may define a layer of a medical device, with each filament of the plurality of filaments extending a distance in a Z-axis to define a thickness of the layer. Each filament may utilize the liquid rope-coiling effect to define a coiled structure. The plurality of filaments may define a lattice structure. The filaments may interlock with adjacent filaments to provide desired properties in X- and Y-axes, with the layer having uniform properties as production parameters are maintained despite the plurality of filaments by which it is defined. A layer so constructed may advantageously be simple to produce while having desired and predictable properties.

A textile is provided over an outer or inner surface or intermediate layer of an elastomeric liner body, and the elastomeric material is used to seal and secure the textile on the liner body. For example, the textile may be placed over the liner body and mechanically interlock with the elastomeric material of the liner body impregnates the textile, and a discrete portion of elastomeric material is used to close the textile material about the liner body, removing any stitching. This feature is advantageous because the embodiment can avoid uncomfortable pressure points by eliminating seams and stitching. This feature is also advantageous because the textile can be attached to the liner body over many points on the textile, ensuring a strong, durable bond. The manufacturing process is also simplified by the removal of the separate stitching procedure.

Because of the controllability of forming the liner according to the structure described above, versatility is provided in forming custom-fitted liners having a variety of features, which are integrally formed or secured to one another. The liners may be custom formed by a lay-up of compatible materials having different yet compatible properties to accommodate uniquely shaped residual limbs.

As the disclosure is not limited to liners, other medical devices may be formed by medical-grade elastomeric materials, such as silicone, according to principles described from discretely and continuously deposited elastomeric material. These medical devices may be prosthetic or orthopedic parts, medical implants, medical tubing, prostheses, and other parts or devices employing such medical-grade elastomeric materials.

These and other features of the present disclosure will become better understood regarding the following description, appended claims, and accompanying drawings.

BRIEF DESCRIPTION OF THE DRAWINGS

FIG. 2G is a plan view of a variation of the center section in the sectional view of FIG. 2C.

FIG. 3A is a perspective cross-sectional view of the liner of FIG. 1 taken along line III-III.

FIG. 3B is a detailed sectional view taken from FIG. 3.

FIG. 4 is a plan view of a layer of the liner of FIG. 1.

FIG. 5 is a perspective cross-sectional view of the layer shown in FIG. 4 taken along line V-V.

FIG. 6 is a plan view of layers of a liner according to an embodiment.

FIG. 10A is an elevational view of a liner according to another embodiment.

FIG. 10B is a detail view 10B of the liner of FIG. 7.

FIG. 10C is a cross-sectional view along line 10C-10C of a filament in the liner of FIG. 10B.

FIG. 13A is a plan view of another embodiment of a layer formed from an elastomeric material.

FIG. 13B is an elevational view of the layer of FIG. 13A.

FIG. 13C is a detail view taken from detail 13C of FIG. 13A.

FIG. 13D is a detail view taken from detail 13D of FIG. 13B.

Figure 1:
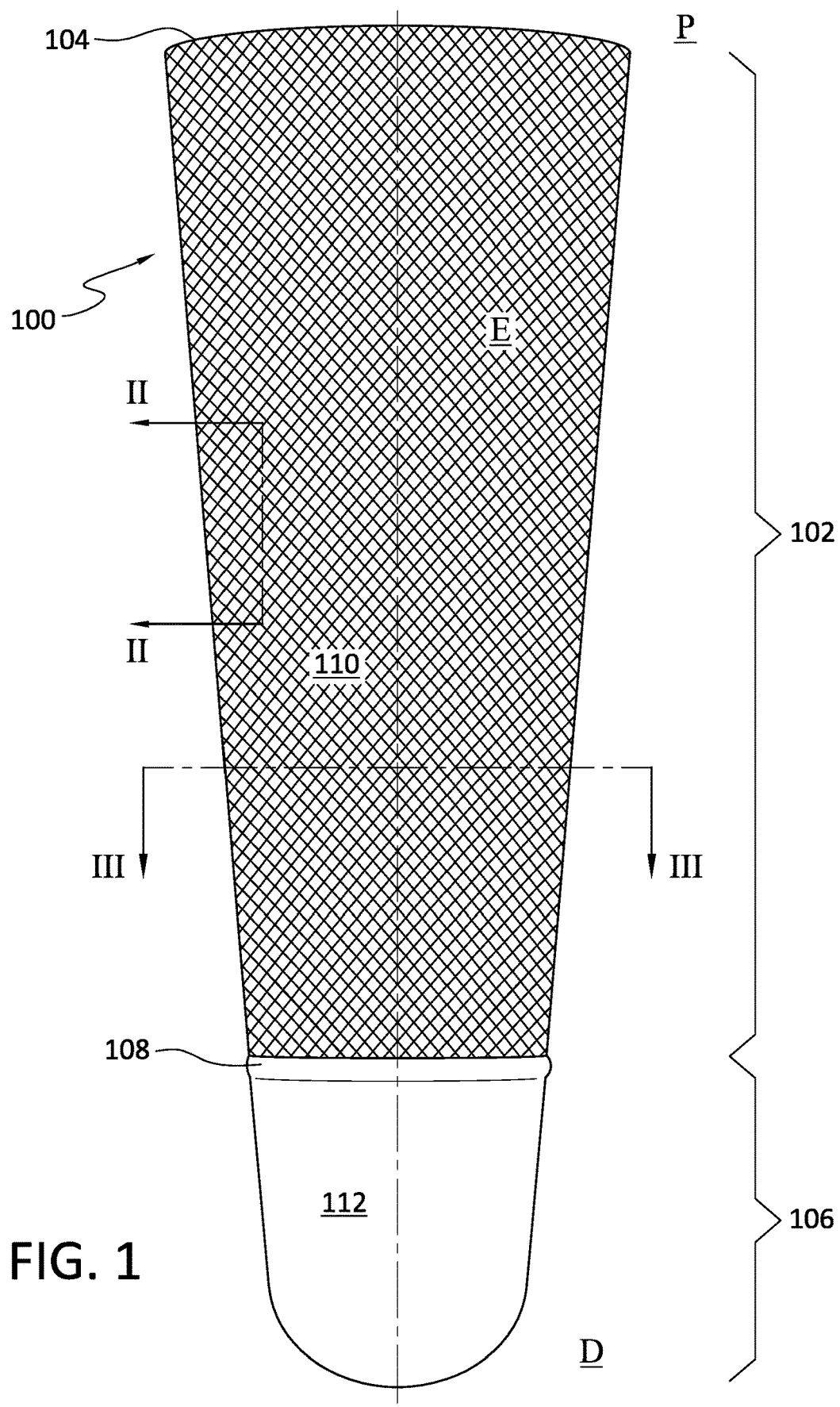
FIG. 1 is an elevational view of a liner according to an embodiment.

The drawing figures are not necessarily drawn to scale, but instead, are drawn to provide a better understanding of the components, and are not intended to be limiting in scope, but to provide exemplary illustrations. The figures illustrate exemplary configurations of a medical device including a lattice or solid structure, and in no way limit the structures or configurations of a medical device and components thereof according to the present disclosure.

DETAILED DESCRIPTION OF VARIOUS EMBODIMENTS

Embodiments of a liner overcome limitations of existing liners by providing a liner structure that advantageously allows for breathability, minimizing the buildup of heat and moisture, without sacrificing the robustness, cushioning, strength, and other advantageous features of solid-walled liners. The liner provides for discrete zones of different features that better address the needs of individual users and the shapes and needs of different residual limbs.

Embodiments according to the disclosure are not limited to a liner, but the liner is merely provided as an exemplary medical device created according to the principles of the present disclosure. Methods and apparatuses that may make devices according to the principles of the disclosure are described in the co-pending U.S. application no. [ ] entitled "ADDITIVE MANUFACTURING SYSTEM, METHOD AND CORRESPONDING COMPONENTS FOR ELASTOMERIC MATERIALS,"

According to the methods and systems of the co-pending application, partially cured or uncured medical-grade elastomeric material, such as silicone, is sequentially deposited onto a substrate by a nozzle or similar device from a material source in a controlled manner according to computer control to define a definitive shape, such as an elongate or continuous filament. The deposited elastomeric material may be a thermoset material such as a silicone or a thermoset polyurethane, resulting in curing after it has been deposited from a nozzle. The additive manufacturing system of the co-pending application can deposit elastomeric material with a preferred blend of elastomeric materials to attain a preferred property at a desired location along or within a medical device so a continuous filament may have different properties, compositions, and shapes at different locations along its length.

An exemplary liner 100 having a ventilated structure formed from a plurality of discretely deposited elastomeric materials in filaments is depicted in FIGS. 1 and 3A. The term discrete, and variations thereof, is intended have its ordinary meaning of being individually separate and distinct. The liner 100 comprises a proximal P or open first end portion 104 into which a residual limb is inserted, and a distal D or closed second end portion 106 arranged proximate a distal D or extreme end of the residual limb. The first end portion 104 and the second end portion 106 define the extreme ends of a liner body 102 which may taper in diameter toward the second or distal end to a solid-walled structure 112. The liner body 102 and the solid-walled structure 112 define an inner cavity 114 contoured to receive a residual limb. An exterior E surface of the liner 100 may be configured to interface or interact with a prosthetic socket, while an interior surface I of the liner 100 may be configured to abut and cushion against a residual limb.

The elastomeric material according to the embodiments herein is discretely deposited as filaments in the sense that each filament is individually, separately, and distinctly formed. While abutting layers or filaments may form a solid and unitary structure, such structure comprises such discretely deposited elastomeric material in contradistinction to a mass of elastomeric material injected into a mold without distinction of discretely composed filaments or similar structures and deliberate properties at specific locations.

According to the embodiments, the elastomeric material is continuously deposited in the sense that a layer or filament is formed without interruption until it has reached an individual length. There may be varying lengths of filaments adjacent or proximate to one another in a structure, such as in an apertured or ventilated structure. The length of a filament may be short, such as but not limited to, 0.1 mm or longer, such as 1 m.

Either way, the elastomeric material is continuously formed as a filament from a discrete mass of material having a predetermined solid cross-section and a predetermined and continuous length that combines with other filaments to make the definitive structure of a liner or other medical device. This feature is advantageous because it allows for a high-level of customization of these structures. The properties of the filaments may be varied and chosen to attain any suitable final product. In embodiments, the size, diameter, and other properties may vary to arrive at a thin film-like layer; in others, the properties of the filaments may cause a thick and/or textured layer of adjoined and identifiable discrete filaments.

The liner body 102 may have a tubular configuration or a conical configuration in certain embodiments, and advantageously defines a ventilated structure 110 allowing the liner 100 to be breathable and permeable to fluids, including moisture, and by consequence heat. The advantageous components and structure of the ventilated structure 110 allow for breathability and permeability of fluids without sacrificing the robustness, mechanical strength, and cushioning offered by solid-walled liners, as described in greater detail below.

In contrast to the ventilated structure 110, the solid-walled structure 112 may be configured with an additional thickness relative to the liner body 102 at the distal end portion 106. The additional thickness of the distal end 106, having a closed configuration, provides additional cushioning at the distal end of the residual limb to support the user's weight. The solid-walled structure 112 also maintains an area of the liner 100 that can create suction against the residual limb, counteracting any loss of suction that existing breathable liners have experienced; whereas mechanical adhesion to the skin may otherwise be relied upon, the solid-walled structure 112 advantageously provides a secure attachment between the liner 100 and the limb. While "solid," the solid-walled structure 112 comprises a plurality of discrete filaments directly adjacent and bonded to one another without a gap between to form the "solid" wall structure, in contrast to a lattice structure forming a plurality of cells or cellular configuration described below, adjacent in an X-axis with the filaments generally aligned in a Y-axis, as depicted in FIG. 12C. The solid-walled structure 112 may, in embodiments, have a durometer of between approximately 30 and approximately 60, and preferably approximately 39-51 Shore 00. The solid-walled structure 112 may further comprise a thixotropic agent for structural stability during a manufacturing procedure.

In the embodiment of FIG. 1, the distal end portion 106 defines a solid and impermeable wall thickness along an entirety of the solid-walled structure 112. The "solid" structure could be considered a film, and a thickness thereof may be modified according to desirable material properties. While defined as a plurality of filaments directly adjacent and bonded to one another in a plane due to the closeness of their proximity, the solid-walled structure 112 may define a plurality of layers adjacently stacked over each other in a Z-axis, as shown in FIG. 12B. The solid-walled structure 112 may also provide additional strength and rigidity for a pin attachment, for example, allowing the pin structure connecting the liner 100 and a corresponding socket to remain in firm engagement with each other without the risk of damage to the liner 100.

The ventilated structure 110 and the solid-walled structure 112 are preferably formed together as a monolithic structure from a plurality of discretely deposited layers of elastomeric material filaments chemically bonded to one another. In this manner, the liner 100 is monolithically formed and acts mechanically as a single object intractably indivisible. This arrangement ensures a durable bond between the liner body 102 and the distal end portion 106. Although both may be preferably monolithic in structure, the ventilated structure 110 and the solid-walled structure 112 preferably have different mechanical properties, such as tensile strength, elasticity (in radial and axial directions), and hardness. This provides an ability to create a product to fit a patient's individual needs. The ventilated structure 110 and the solid-walled structure 112 may be individually formed and secured together mechanically and/or chemically, such as by adhesives, and allows for production flexibility and using different materials and processes.

The liner body 102 and the solid-walled portion 112 may be formed from one or more elastomeric materials. Either or both of the liner body 102 and the solid-walled portion 112 are preferably formed from a medical-grade elastomer. Such medical-grade elastomeric materials preferably include silicone, polyurethane, or other elastomeric material. For the disclosure, the embodiments will be described as formed from medical-grade silicone. Examples of medical-grade silicone and other elastomeric materials are obtainable from NuSil Technology of Carpinteria, Calif., under product designations CF13-2188, MED-4901, MED-6340 or MED-6345, the datasheets associated with each of these exemplary silicone materials being incorporated herein by reference. Other silicone compositions can be used, and the embodiments herein are not limited to the exemplary silicone materials, but rather may be formed from other suitable polymeric or elastomeric compositions such as polyurethane, block copolymer, etc.

The liner body 102 may be formed of a different material or one having different properties than the solid-walled portion 112, and individual layers, including a first layer 122 of the liner body 102, may have a different material than material found at the second end portion 106. Materials forming the first layer 122, the liner body 102, the second end portion 106, or combinations thereof may comprise the same material but may be configured to have different structural and functional properties.

An interface 108 may provide a robust attachment between the ventilated structure 110 of the liner body 102 and the solid-walled structure 112 of the distal end portion 106. The interface 108 may comprise an added layer of elastomeric bonding between components of the solid-walled structure 112 and the ventilated structure 110. The liner body 102 and the distal end portion 106 are preferably integrally formed with and chemically bonded to one another. The liner body 102 is secured along the interface 108 to the solid-walled structure 112 by chemical bonding between the material forming the liner body 102 and the material forming the solid-walled structure 112. The materials of the ventilated structure 110 and the solid-walled structure 112 may be blended at the interface 108, which may be minimal in thickness or extension and merely comprise portions of each the ventilated structure 110 and the solid-walled structure 112. The degree at which the blending at the interface occurs may be minimal so as not to alter the shape of the filament, but sufficient to assure bonding of the adjacent portions of the filaments.

Figure 2A:
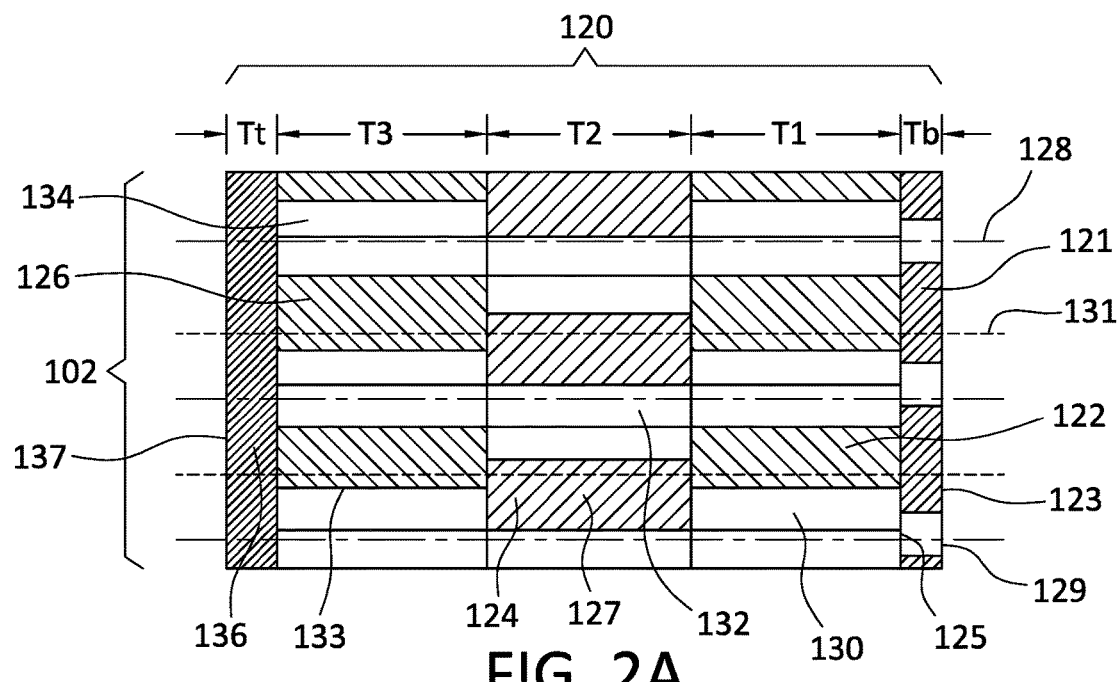
FIG. 2A is a perspective cross-sectional view of the liner of FIG. 1 taken along line II-II.

Turning to FIG. 2A, a wall thickness 120 extends between a base layer 121 and a layer 136. The layer 136 is arranged on an outwardly facing surface of the liner 100 and is configured to interface with a corresponding prosthetic socket. The layer 136 may be formed by a textile or an alternative to a textile. The layer 136 may be formed by a plurality of filaments that define a fine pattern imitating a semi-closed surface, such as in a textile. The fine layer of filaments may be formed from an elastomeric material having a friction-reducing coating. And the fine layer of filaments may have a composition mixed with the elastomer, such as Parylene C, which is a chemical vapor deposited as poly(p-xylylene) polymers used as moisture and dielectric barriers. The base layer 121 is arranged on an inwardly facing surface of the liner 100 and configured to interface with the residual limb. Multiple layers 122, 124, 126 may extend between the base layer 121 and the textile 136. Each layer 121, 122, 124, 126, 136 has unique properties and features, which allows for a high degree of customization corresponding to the user's dimensions and needs.

In an embodiment, the base layer 121 may be configured as a substantially solid film of elastomeric material formed from joined filaments and extending over and around a residual limb. A benefit of this arrangement is an optimized frictional engagement with the skin at an inner surface 123 of the base layer 121 to prevent pistoning, milking, or catastrophic failure of the prosthetic system due to poor engagement between the residual limb and the liner 100.

The base layer 121 may comprise apertures or openings 129 arranged in a predetermined pattern and preconfigured shape in a fixed manner, as described below, referring to FIG. 2B. The openings 129 are arranged fixedly to assure the openings 129 intersect or correspond to other layers and corresponding openings in the thickness of the liner body 102. The openings 129 may advantageously extend through an entirety of a thickness Tb of the base layer 121. In an embodiment, the openings 129 may align with and define a portion of an interstice axis 128 extending through the thickness 120 of the liner body 102, providing a substantially direct channel or passage through which fluid and heat may pass from the residual limb through each layer 121, 122, 124, 126, 136 to the exterior E of the liner 100.

An inner surface 123 of the base layer 121 defines the inner cavity 114 of the liner 100, and comprises a solid surface area greater than a cumulative surface area of openings 129, to provide an effective and reliable skin interface. The solid surface should be smooth because it generally has a uniform elevation aside from the openings 129. The smooth surface avoids pressure points against the skin of the user and assures even adherence to the skin of the residual limb for effective frictional engagement. The base layer 121 defines a generally uniformly arcuate and/or circular profile, as it conforms to and defines the tubular shape of the liner body 102. The inner surface 123 may be flat if arranged in a planar configuration, due to the properties of the smooth surface. The arcuate and/or circular profile mitigates pressure peaks or points and absorbs shear forces during use, protecting skin and possible scar tissue of a residual limb.

The inner surface 123 may be additionally prepared with an active skincare additive for enhanced comfort and skincare and for easier donning and doffing. The skincare additive may be silicone oil, Vaseline®, menthol, antimicrobial compositions, aloe vera, or any other suitable skincare additive to mitigate irritation, dermatological issues, or mechanical issues. For example, the base layer 121 may comprise a composite material including silicone elastomer and silicone oil dispersed through the silicone elastomer, and/or the base layer 121 may contain a plurality of hollow microspheres of silicone oil or other additive dispersed through the silicone elastomer.

The base layer 121 is preferably formed by a plurality of discretely deposited filaments or material depositions to form its structure. Aside from the openings 129, the base layer 121 is preferably solid-walled, and the filaments abut the filaments adjacent to one another to form such a solid-wall structure. The deposition of the filaments is controlled, in that certain filaments may be interrupted in deposition, to form the predetermined shape of the openings 129. This advantageously provides a controlled and clean plurality of openings 129 and also simplifies the manufacturing process by mitigating the need for negative removal or "punching out" of material to form the openings after formation of the base layer.

As in the embodiments herein, the filaments can have different sizes and shapes relative to another. According to certain embodiments, the filaments have a circular cross-section, but they may have other shapes and cross-sections according to the deposition equipment used to deposit the filaments. Such cross-sections may include predetermined shapes such as square, rectangle, triangle, circular oval, etc., as the shapes are only restricted by the equipment employed for filament deposition. An embodiment or certain layers need not have filaments consistently of the same shape, but may have variable shapes according to the desired properties and form of the embodiment or layers. The cross-sections need not by symmetric and may change along a length of the filament.

The dimensions of the filaments can be modified appropriately according to the desired properties of a layer. For example, the filaments can have an exemplary precise diameter of 0.1 mm or be arranged in a rectangular form of 1 cm×2 cm. The ability to precisely control the size enables variable structures in the liner, and to a greater extent of a medical device. The filaments may have different predetermined lengths relative to one another to form precise surface features (i.e., openings) in a certain layer, or may be stacked along other layers to form precise surface elevations or protruding elements. For an example, a volume control pad may be formed along the inner surface of the liner by gradual deposition of filament segments stacked upon one another in different lengths and a predetermined protruding shape in FIG. 14.

The base layer 121 may have a durometer ranging from approximately 40 Shore OO to approximately 50 Shore OO, and may vary from a top end to a lower end; at a lower end proximate a user's skin, the durometer may be in certain embodiments approximately 45 Shore OO, whereas at a top end opposite the lower end, the durometer may be higher, preferably approximately 50 Shore OO. The base layer 121 may have a tensile strength at the top end of between 2 and 6 N at 100% elongation, and preferably approximately 4 N at 100% elongation. The lower end may have a tensile strength of between 0.5 N and 4 N at 100% elongation, and preferably approximately 2 N at 100% elongation.

In embodiments, the base layer 121 may be a textile layer. The textile layer may be provided on a surface, such as an inside surface, thereof with an elastomeric material that facilitates skin adhesion by providing frictional features and other properties. The elastomeric material on the inside surface of the textile layer may be interlocked with the textile material (for example, by bleeding into and curing against the textile material) and may define any suitable pattern. For example, the pattern may be a mesh pattern, a grid pattern, repeating shapes, dots, or other formations that may define frictional and skin-engaging features. The pattern defined by the elastomeric material on the surface may cumulatively comprise approximately half of the surface area of the base layer 121. The depicted embodiment is merely exemplary and is not limiting.

A first layer 122 may be formed from silicone and arranged adjacent to and concentric with the base layer 121 and may attach to the base layer 121 through chemical bonding, adhesives, or any other suitable attachment mechanism. In an exemplary embodiment, an innermost portion or surface of the first layer 122 is chemically bonded to the base layer 121 at a junction 125, with the integral formation of the base and first layers 121, 122 allowing the layers 121, 122 to have different properties and structures but to be reliably and permanently secured to one another to prevent separation under loads and to retain the mechanical advantages of solid elastomeric liners.

The first layer 122 may be formed of a material having different or the same mechanical properties as the base layer 121, although arranged in a different structure than the base layer 121. For example, while the filaments defining the base layer 121 may define a substantially laminar or solid film of soft silicone perforated or interrupted by the openings 129, the first layer 122 may be formed from filaments, strands, ribs, or other structures that allow for a plurality of substantial openings 130 to be defined in and through a thickness of the first layer 122. The first layer 122 may have a higher durometer or hardness than the base layer 121. In certain arrangements, the first layer 122 comprises a higher stiffness than the base layer 121. The increased stiffness enables the first layer 122 to provide stability, such as through circumferential and axial elasticity, while the softer base layer 121 provides shock absorption, comfort, and frictional engagement with or against the residual limb.

The openings 130 preferably define a predetermined pattern and predetermined shape. The openings 130 correspond to and are aligned to be coaxial or overlap with the openings 129 of the base layer 121, and coinciding with the interstice axes 128. The openings 130 may extend through an entire thickness T1 of the first layer 122. A thickness T1 of the first layer 122 may be greater than a thickness Tb of the base layer 121, with the increased thickness T1 providing strength and mechanical support to the liner 100 while the openings 130 reduce overall weight and bulk. The openings 130 may comprise a different shape than the openings 129 and may have a different surface area. For instance, the openings 130 may be larger or smaller than the openings 129, and the combined solid surface area of the first layer 122 may be less than a combined surface area of the openings 130, in contrast to the base layer 121.

In embodiments, the base layer 121 may, in an unstretched state, comprise between approximately 5% and approximately 15% of its surface area as open areas, for example, defined by the openings 129. The first, second, and third layers 122, 124, 126 may be formed so between approximately 30% and approximately 70% of a surface area of the first, second, and third layers 122, 124, 126 is open area, and preferably between 40% and 60%. The percentages are merely exemplary and may change based on a load applied to the liner 100 or based on the dimensions of a user wearing and using the liner 100.

The filaments, strands, ribs, or other structures forming the first layer 122 may additionally be formed from a material having different properties than the material forming the base layer 121. While the base layer 121 may define a frictional material, for example, the first layer 122 may comprise a material having a lower durometer than the base layer 121, greater elasticity, anisotropic elastic properties, or enhanced heat transfer characteristics. These characteristics are exemplary, and the material forming the first layer 122 may comprise any number or combination of other advantageous properties.

A second layer 124 may be formed from silicone or another elastomeric material and arranged adjacent to and concentrically with the first layer 122. The second layer 124 may possess the same or different properties and structures compared to the base and first layers 121, 122. As exists between the first and base layers 122, 121, an innermost portion of the second layer 124 may be integrally formed and/or blended with an outermost portion of the first layer 122, preferably by chemical bonding. The integral formation of the materials of the first and second layers 122, 124 allows the layers to be reliably attached during the liner 100, which provides the benefits of a solid-walled structure and to still maintain distinct properties and structures.

The second layer 124 may define structures 127, such as filaments, strands, ribs, or other structures having a thickness T2, through an entirety of which a plurality of apertures or openings 132 may be defined. The apertures 132 are formed from interrupted segments of filaments in the continuous direction of the second layer 124 and the filaments that define it. The openings 132 may be advantageously arranged as coaxial or overlapping with the openings 129, 130 of the base and first layers 121, 122, and may have a predetermined shape and a predetermined pattern, as in the base and first layers 121, 122.

The openings 132 further define and extend along the interstice axes 128, and form a substantially direct channel for moisture and heat to escape from the interior I of the liner 100. In embodiments, the openings 132 may be staggered relative to the openings 130 of first layer 122. The staggered relationship of the structures 127 and the openings 132 relative to the openings 130 and structure of the first layer 122 advantageously allow for columns 131 of solid structures to extend continuously between the inner surface 123 of the base layer 121 to an outer surface 137 of the textile 136. The columns 131 are formed because at least some of the filaments from layers 121, 122, 124, 126, and 136 overlap along an axis from the inner surface I to the exterior surface E. The columns 131 may provide mechanical strength and cushioning when the outer surface 137 of the textile 136 contacts and receives a load from a corresponding prosthetic socket.

As with the first layer 122, the second layer 124 may have different properties than the base layer 121 and the first layer 122. For example, the second layer 124 may have increased stiffness, increased elasticity, anisotropic elasticity, or any other property that complements the cushioning effect of the base layer 121 and the properties of the first layer 122. Another consideration is the liner 100 may become more ventilated as the liner 100 is distended, as the ventilated structure 110 enlarges and expands the openings of the layers 121, 122, 124, 126, 136.

An exemplary third layer 126 may be formed from an elastomeric material and arranged adjacent to and concentric with the second layer 124. Similar to the base, first, and second layers 121, 122, 124, the third layer 126 may be adhered to the second layer 124 by chemical bonding, adhesives, or any other suitable attachment method. In preferable chemical bonding, there is blending of an innermost portion of the third layer 126 with an outermost portion of the second layer 124, so the second and third layers 124, 126 are integrally formed and fixedly joined, yet retain distinct properties.

The third layer 126 may define structures 133 comprising filaments, strands, ribs, or any other structure that may define a plurality of openings 134 extending through a thickness T3 of the third layer 126. As with the other layers, the openings 134 may have a predetermined shape and may be arranged in a predetermined pattern. The openings 134 may be arranged to at least partially correspond to the openings 132, 130, 129 of the other layers, and extend along with the interstice axis 128. As with the second layer 124, the structures 133 of the third layer 126 may be arranged in size and shape to at least partially overlap with and abut the structures 127 of the second layer 124, extending and defining the columns 131 for radial strength and stability.

The first, second, and/or third layers 122, 124, 126 may individually or in combination define a center section of the liner body 102 and may be provided to have a durometer of between about 20 Shore A and about 60 Shore A, and preferably approximately 40 Shore A. The center section may have a tensile strength of between about 1000 psi and about 1600 psi, and preferably approximately 1350 psi, and thixotropic properties to retain a desirable or predetermined shape.

It will be appreciated that additional layers may be provided adjacent to and concentric with the base, first, second, and third layers 121, 122, 124, 126, and other structures or layers may discretize one or more of the base, first, second, and third layers 121, 122, 124, 126 from the other layers. For example, a matrix of stiffening material extending longitudinally from the distal end portion 106 may extend between the first and second layers 122, 124. The matrix may provide additional mechanical strength in axial or radial directions. The layers 121, 122, 124, 126 may extend entirely to the distal end portion 106 of the liner 100 without interruption by the solid-walled portion 112. The distal end portion 106 may comprise structures such as an umbrella connector, additional layers having additional cushioning, spacer materials, wicking materials, or other components.

In embodiments, a second base or skin-facing layer may be provided immediately adjacent to the base layer 121 and between the base layer 121 and the first layer 122. The second base layer may comprise the same material as the first, second, and/or third layers 122, 124, 126, and may preferably be defined by thinner filaments. The second base layer may provide support and strength for the base layer 121.

Each layer may have different mechanical properties and may be formed from different materials, although such materials are compatible to permit chemical bonding. For example, the second or third layers 122, 124, 126 may have greater stiffness or hardness, as the more inward layers, e.g. layers 121, 124, have lower hardness and greater compressibility. It will be appreciated that the arrangement of the structures and openings of each layer 121, 122, 124, and 126 may vary circumferentially as suitable, and also may vary axially. For instance, the depicted arrangement with the columns and the interstice axes may be well-suited to a particular portion of a liner or medical device; while another embodiment (e.g. in which a greater or smaller number of openings may be provided and may be differently aligned with the structures and openings of adjacent layers) may be suited to a different region. In embodiments, the structures of layers may be arranged adjacent an opening of an adjacent layer rather than defining the columns.

Each layer 121, 122, 124, 126, 136 may have a different thickness as suitable for a particular user, for a particular application, or otherwise. In embodiments, the base layer 121 may have a thickness ranging from 0.1 mm to 1 mm, and may preferably have a thickness of approximately 0.5 mm. The second base layer may have a similar thickness as the base layer 121, for example, 0.5 mm. The first, second, and third layers 121, 124, 126 may have thicknesses of 0.1 to greater than 1 mm, and may preferably have a larger thickness than the base layer 121. In embodiments, the first, second, and third layers 121, 124, 126 may have a thickness of approximately 0.7 mm. The textile layer 136 may have a thickness of 0.1 to 1 mm, with a preferred thickness of approximately 0.5 mm, and may be attached to an adjacent layer by an adhesive having a thickness of 0.05 to 0.2 mm, and preferably of about 0.1 mm. A total thickness of the liner body 102 may be approximately 3 to approximately 6 mm, with a preferred thickness of approximately 4-5 mm. The dimensions described are not limiting and are merely exemplary.

A lattice structure formed by the interstices 129, 130, 132, 134 can be varied among different layers and in different coordinates of a layer itself or in correspondence with other layers. For example, a rib may be formed by the layers at a predetermined location of the circumference of the liner 100 and generally extend axially between the first and second end portions 104, 106 of the liner 100. The lattice structure at the rib may comprise of the interstices as being smaller relative to other interstices, or may not exist with the filaments of each sub-layer abutting one another to form the rib, but spaced beside one another outside the rib.

A fabric or textile material may form a textile layer 136 at an outward-facing portion or periphery E of the liner 100. The textile layer 136 may be secured against an immediately adjacent layer, such as the third layer 126, by impregnation of the material of the textile layer 136 with elastomer from the third layer 126. The third layer 126 may be attached via adhesives or any other suitable attachment mechanism to the textile layer 136. The third layer 126 may impregnate the textile layer 136 at portions corresponding and adjacent to the structures 133, leaving portions of textile layer 136 corresponding and adjacent to openings 134 unimpregnated by the elastomeric material.

The textile layer 136 may be configured for interfacing with a corresponding prosthetic socket, for resisting wear and tear, for providing desired properties regarding anisotropy or moisture wicking, for absorbing moisture, for providing desired levels of stiffness in a certain axis such as to control pistoning, or for facilitating donning and doffing of the liner 100. The textile material may modify stretching of the liner body 102, for example by increasing radial stretch of the liner body 102 and offering counteracting elasticity to the liner body 102 by having a different elasticity than one or more layers 121, 122, 124, 126. Further, the textile material may facilitate breathability. The textile layer 136 may comprise functional zones defined by distinct sections of knitted patterns that impart certain shapes, elasticities, stiffnesses, or tendencies to the liner 100.

The textile layer 136 may be formed of a breathable material, so the fluid and heat flowing through channels defining the interstice axes 128 may diffuse or bleed through the textile layer 136 to an exterior of the liner 100. Because the material of the third layer 126 impregnates the textile layer 136 only at portions of the textile layer 136 corresponding and adjacent to the structures 133, portions of the textile layer 136 corresponding to the interstice axes 128 remain breathable and permeable to fluid and heat, while the textile layer 136 remains firmly attached to the liner body 102. The textile layer 136 may have a thickness Tt that is less than a thickness T1, T2, T3 of the first, second, and third layers 122, 124, 126.

Due to the elasticity of elastomers such as silicone or other materials forming the layers 121, 122, 124, 126, the openings 129, 130, 132, 134 defined through the layers 121, 122, 124, 126 may distend upon donning of the liner 100, as the residual limb forces the layers 121, 122, 124, 126 to assume a larger circumference and to cover a greater surface area than in a contracted resting condition of the liner 100. As the openings 129, 130, 132, 134 distend and enlarge upon donning due to the materials forming the layers 121, 122, 124, 126 spreading apart, permeability of the liner 100 to fluid and heat may increase, while the solid structures defining layers 121, 122, 124, 126 may continue to provide structural and mechanical strength and comfort to the residual limb from pressure points, contact with the prosthetic socket, or otherwise. The thicknesses Tb, T1, T2, T3, Tt of the layers may decrease as the liner 100 expands and distends, and the structures may be continued to define the columns 131, providing strength and support.

The layers 121, 122, 124, 126 and the textile layer 136 together define the thickness 120 of the liner body 102. FIG. 3A depicts a perspective cross-sectional view of the liner 100. The inner cavity 114 is surrounded by concentric layers 121, 122, 124, 126, 136. The concentric layers 121, 122, 124, 126, 136 extend through an entirety of the liner body 102 and comprise different materials and/or different properties to define a comfortable, robust, and breathable liner 100. It will be understood that the liner body 102 may comprise discrete or tapered sections comprising different layers and different materials from the embodiment shown, which is exemplary and non-limiting.

Figure 2B:
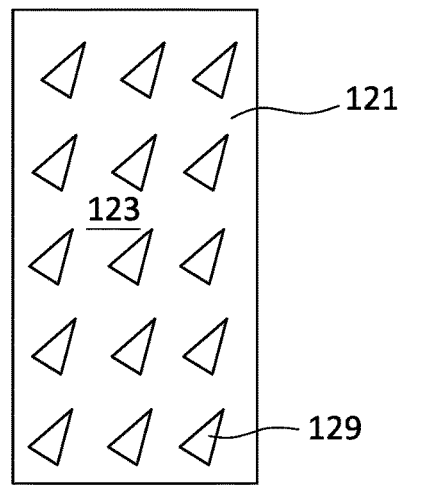
FIG. 2B is a plan view of a base of the liner of FIG. 1.

FIG. 2B a detailed view of the base layer 121. The base layer 121 defines the inner surface 123 of the liner 100 and the plurality of openings 129. The openings 129 are not limited in shape and may be formed in many geometric shapes suitable for facilitating the flow of air and sweat. The openings 129 may be distributed in a non-uniform pattern, with a greater density of openings 129 in areas where greater flexibility and/or breathability is desired, and with a lower density of openings 129 in areas where less flexibility or less breathability is desired.

Figure 2C:
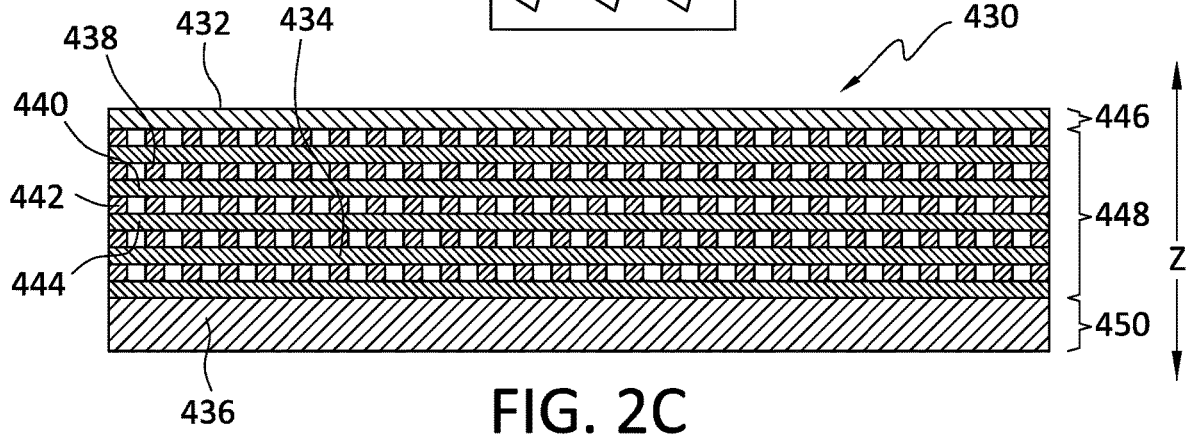
FIG. 2C is a perspective sectional view of a variation of the liner of FIG. 2A.
Figure 2D:
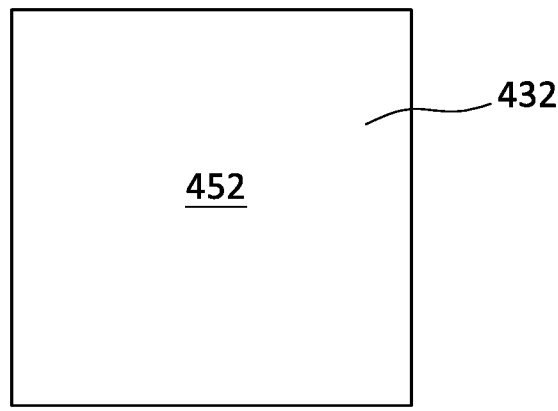
FIG. 2D is a plan view of a base layer in the sectional view of FIG. 2C.
Figure 2E:
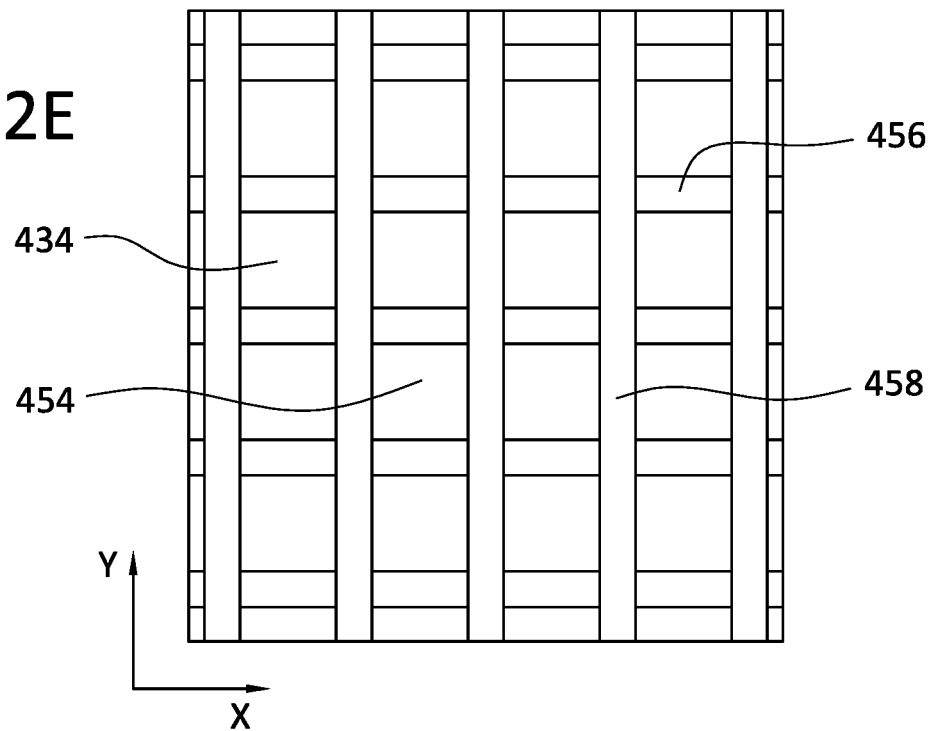
FIG. 2E is a plan view of a center section in the sectional view of FIG. 2C.
Figure 2F:
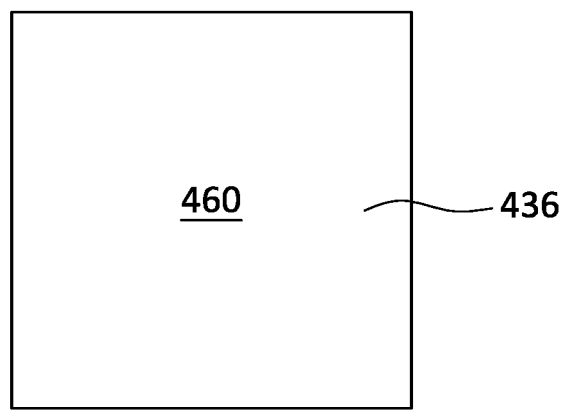
FIG. 2F is a plan view of a textile layer in the sectional view of FIG. 2C.

FIGS. 2C-2G show a variation of the liner structure of FIG. 2A. A liner structure 430 in FIG. 2C may comprise a base layer 432 having an apertured structure 452 in FIG. 2D. A center section 434 may comprise at least two layers 438, 440, 442, and 444, arranged in a grid-like configuration and stacked over each other in alternating X and Y directions, as shown in FIG. 2E. For example, at least two layers have filaments 456 extending over each other in an X-axis, and spaced apart by each other in a Z-axis by filaments 458 extending in a Y-axis. It has been found that stacking filaments parallel with one another in the Z-axis creates a significantly cushioned center section 434. Stacked filaments staggered relative to one another in the Z-axis (exemplified in FIG. 6) may provide less cushioning. FIG. 2F shows an outer layer 436 as having a ventilated structure 460, so a transfer of air and other fluids is created from the base layer 432, through the center section 434 and through the outer layer 436. The outer layer 436 may be an elastomeric layer formed by filaments, a textile layer, or any other suitably formed structure.

Referring to FIG. 2C, the base layer 432 may have a substantially thinner thickness 446 than a thickness 448 of the center section 434. The base layer 432 may be formed from a single layer of filaments or a plurality of filaments. The center section 434 comprises a plurality of the filaments, and each filament may be selected to have a thickness greater than or less than the total thickness 446 of the base layer 432. At least in the depicted embodiment, the center section 434 has a total thickness 448, defined as a combination of each layer of filaments, and is substantially greater than a thickness of base layer 432. For example, by "substantial," it is meant that the center section thickness 448 may be at least twice the thickness 446 of the base layer 432. The outer layer 436 preferably has a thickness 450 greater than the thickness 446 of the base layer 432, but less than the thickness 448 of the center section 434, as the center section 434 is arranged to serve as the primary cushioning feature of the liner structure 430.

FIG. 2G is a variation of FIG. 2E in that a first layer of filaments 462 extend in a first direction, a second layer of filaments 464 extends in a second direction different and relative to the first direction. For example, the first and second layers of filaments 462, 464 extend in oblique angles relative to the X and Y axes, forming vertices 468. The vertices 468 can be any number of desirable angles, such as those represented in FIGS. 7A-7D. In the depicted embodiment, the first and second layers may extend obliquely relative to the x and y axes and at right angles or perpendicularly to each other. A third layer of filaments 466 may be vertically arranged along the Y-axis and may bisect the vertices 468, or may be offset from the vertices 468. By arranging a layer of filaments 466 relative to the first and second layers of filaments 462, 464, this third layer of filaments 466 may be disposed to facilitate or inhibit elongation in a direction relative to the X-Y axis.

In a variation, the third layer or the layers of filaments may comprise a composite of filaments adjacent and bond to one another. For example, the third layer of filaments may comprise of each filament formed by two filaments each having a different material property to inhibit or facilitate elongation along its length.

FIG. 3B exemplifies vertical flow paths or channels 135 defined through a longitudinal length of the layers 121, 122, 124, 126. The vertical flow paths or channels 135 define openings between solid structures forming the layers 121, 122, 124, 126, and allowing breathability or permeability toward fluids and heat that allows fluids and heat to escape from the residual limb not only in a radial direction but also in a vertical direction. Fluid and heat may be expelled via the vertical flow paths 135 in either a distal or a proximal direction. The vertical flow paths 135 are depicted as extending in an alternating fashion between multiple of the layers 121, 122, 124, 126, but it will be appreciated that vertical flow paths 135 may extend through all layers, select layers, or a single layer, and uniformly or non-uniformly through the layers and the liner body 102.

In the illustrated embodiment of FIG. 4, the first layer 122 comprises sub-layers of structures, which are layers of filaments, together forming the first layer 122. In a first sub-layer 140, a plurality of first filaments 140 extends in a direction D1, with separate first filaments 141, 143 extending parallel to one another and spaced apart a distance d1 as exemplary for the arrangement of the first filaments 140. A second sub-layer 142 adjacent to the first sub-layer 140 comprises a plurality of second filaments 142 defining the second sub-layer 142 and extend in a second direction D2. The second direction D2 may be perpendicular to direction D1 or may extend in any direction relative to the first direction D1. The second filaments 142 may likewise comprise separate second filaments 145, 147 spaced apart a distance d2, and extend parallel to one another.

The second sub-layer 142 is arranged to overlap or underlap the first sub-layer 140 and to define between the first and second filaments 140, 142 the openings 130 corresponding to the predetermined location of interstice axes 128. The arrangement of the first and second sub-layers 140, 142 defines a lattice structure. Each opening or interstice 130 may be arranged to define the interstice axis 128 extending perpendicularly or orthogonally through a thickness T1 of the first layer 122. The distances D1, D2 define the dimensions of the openings 130, as established by spaces between separate filaments 141, 143, 145, 147.

The first sub-layer 140, comprising separate filaments 141, 143, may be arranged within the first layer 122 to be closer to an interior I of the liner 100 than the second sub-layer 142, with the first and second sub-layers 140, 142 comprising different material properties suited for their respective locations. For example, the first sub-layer 140 may comprise a lower durometer, lower tensile strength, greater elongation, or greater tear strength, or may include different skin additives, any of which properties may provide for greater comfort at the residual limb and/or enhanced frictional engagement between the liner 100 and the residual limb particularly owing to the closer proximity of the first sub-layer 140 to the user's skin. The properties of the first and second sub-layers 140, 142 may change throughout the length and circumference of the liner 100.

FIG. 5 depicts a perspective cross-sectional view of an intersection between the first and second filaments 140, 142 of the first layer 122 taken along line V-V in FIG. 3. The first filaments 140 are configured to overlap and extend over the second filaments 142, with discrete intersections 149 of the first and second filaments 140, 142 occurring in a predetermined pattern throughout the first layer 122 according to the first and second directions D1, D2 in which the first and second filaments 140, 142 continuously extend relative to each other. The first and second sub-layers 140, 142 may secure to each other at blended portions 148 at one or more intersections 149, so the filaments of the first and second sub-layers 140, 142 are continuous and contiguous with one another at the intersections 149. If the first and second filaments 140, 142 are formed from silicone or other elastomeric material, the blended portion 148 may comprise a chemical of material at the edges or outermost portions of first and second filaments 140, 142, creating an integrally formed intersection of first and second sub-layers 140, 142. In an exemplary embodiment, the first and second filaments or sub-layers 140, 142 are formed from medical-grade silicone. The bonding or attachment of the filaments 140, 142 at the intersections 149 can ensure that the layer 122 maintains structural integrity and desired mechanical properties.

FIG. 6 depicts an embodiment of the second layer 124 adhered and adjacent to the first layer 122 and the first and second sub-layers 140, 142, to juxtapose both the first and second layers 122, 124 arranged in lattice structures. The second layer 124 comprises third and fourth sub-layers 144, 146, relative to the first and second sub-layers 140, 142, and are arranged in a pattern defining openings and intersections between the third and fourth sub-layers 144, 146. As with the first and second sub-layers 140, 142, the third sub-layer 144 defines distinct and separate filaments 151, 153 extending parallel to each other and spaced apart a distance d3, while the fourth sub-layer 146 defines distinct and separate filaments 155, 157 extending parallel to and spaced apart a distance d4. The distances d3, d4 define the dimensions of openings 132 extending through a thickness of the second layer 124.

The openings 132 are arranged to at least partially correspond with the openings 130 of the first layer 122, so the interstice axes 128 may be defined and extend through a thickness of both the first and the second layers 122, 124. The filaments 141, 143, 145, 147 may be staggered within the first layer 122, and the filaments 151, 153, 155, 157 may be staggered within the second layer 124, and between the filaments of the first and second layers 122, 124. This arrangement advantageously provides channels along interstice axes 128 that may allow the flow of fluid and heat from the residual limb to the exterior E of the liner 100. It will be appreciated that while the first and second layers 122, 124 are described, filaments or other structures may be arranged in additional layers, such as the third layer 126, in similar ways or alternative configurations.

The staggering of the filaments 141, 143, 145, 147 of the first layer 122 and filaments 151, 153, 155, 157 of the second layer 124 further provides beneficial cushioning effects and mechanical strength to the liner body 102. When the liner 100 is donned and used, the liner 100 receives loads owing to the weight of the user bearing down upon the prosthetic socket system, pressing the liner 100 into and against the corresponding prosthetic socket. As the liner 100 presses downwardly and outwardly into and against the socket, the layers 121, 122, 124, 126, and the textile layer 136 may be radially compressed between the socket and the residual limb. The columns 131 of solid material comprising portions of layers 121, 122, 124, 126, and the textile layer 136 advantageously resist compression and provide cushioning to the residual limb, minimizing pressure points against the residual limb while maintaining the interstice axes 128 to enable transfer of fluid and heat.

The columns 131 may further provide relief by means of the staggered arrangement of filaments 141, 143, 145, 147, 151, 153, 155, 157 as the layers 121, 122, 124, 126, and textile layer 136 are compressed by providing that the columns 131 may "lay down" against an adjacent column 131, forming a reinforced or cushioned arrangement of layers of the columns 131. As the liner 100 is compressed, each filament running parallel to each other (e.g., sub-layers 155 and 157) will lean to one side of the sub-layer of filaments below it, causing the column 131 to lean into an adjacent column 131. The ease by which the filaments can be compressed (because the staggered arrangement does not force two or more filaments to be compressed directly on top of one another) is advantageous because it creates a cushioned effect. The proximity of each column 131 to another column 131 will give support because a compressed column which lays down will lean into an adjacent column, spreading the pressure of the compression to a larger area reducing the pressure felt by the wearer.

The filaments of the first and second layers 122, 124 may be formed from different but compatible materials depending on their material properties. Even among the first and second layers 122, 124, the sub-layers 140, 142, 144, 146 may have different mechanical properties which may vary along a length of any of the filaments, while all being permanently joined to one another by chemical bonding.

Figures 7A, 7B, 7C, 7D:
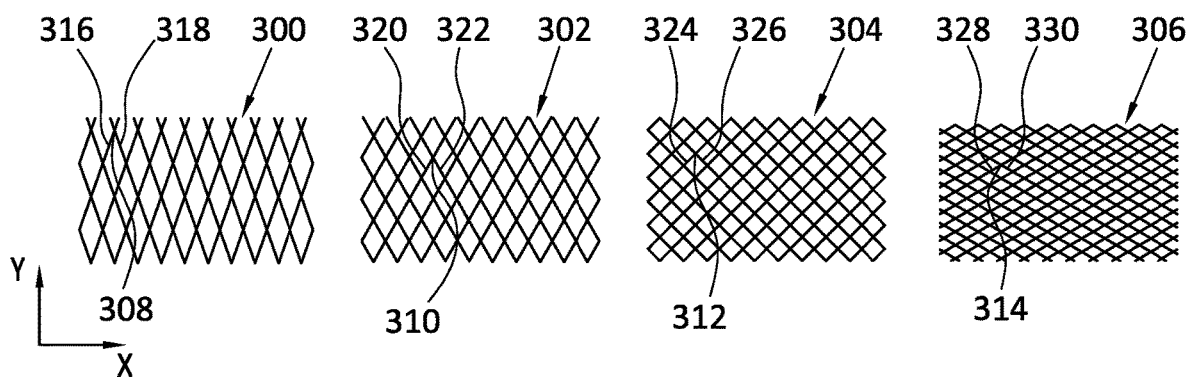
FIG. 7A is a schematic view of a first-line patch pattern having an angle at 20 degrees.
FIG. 7B is a schematic view of a second-line patch pattern having an angle at 30 degrees.
FIG. 7C is a schematic view of a third-line patch pattern having an angle at 45 degrees.
FIG. 7D is a schematic view of a fourth-line patch pattern having an angle at 60 degrees.
Figure 7E:
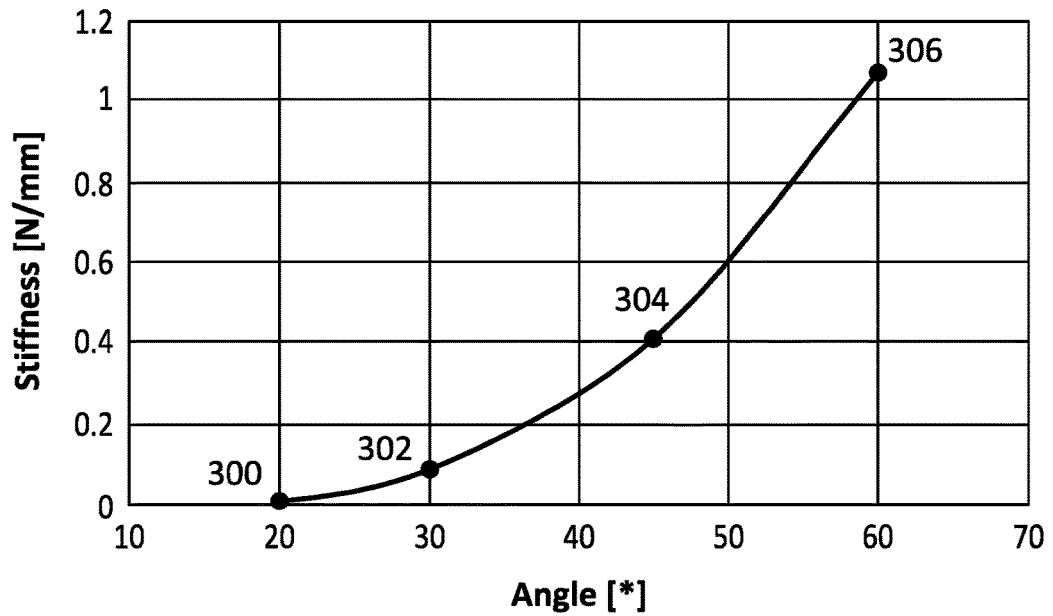
FIG. 7E is a graph plotting angle versus stiffness of the first, second, third, and fourth line patch patterns.

FIGS. 7A-7D exemplify different patterns of layers of filaments, which can change the stiffness or other properties of the combination of the overlapping layers of filaments, as exemplified in FIG. 7E. It has been found that as the angle of the vertices increases, so does the radial stiffness of a corresponding tubular liner, as in FIG. 1. The stiffness can be adapted in localized areas or about an entirety of a circumference of a liner. For example, in a liner, these benefits could be applied to a trans-tibial liner where the localized elastomeric stiffness in the knee area could be reduced, allowing easier knee flexion. Another example could be a gradual reduction in stiffness towards the proximal opening of a liner to improve comfort and to ease donning and doffing of the liner 100.

FIG. 7A shows a layer 300 with first and second filament layers 316, 318, having vertices 308 oriented toward the Y-axis of 20°. FIG. 7B shows a layer 302 with first and second filament layers 320, 322 as having vertices 310 oriented toward the Y-axis of 30°. FIG. 7C shows a layer 304 with first and second filament layers 324, 326 as having vertices 312 oriented toward the Y-axis of 45°. FIG. 7D shows a layer 306 with first and second filament layers 328, 330 as having vertices 314 oriented toward the Y-axis of 60°.

Figure 8A:
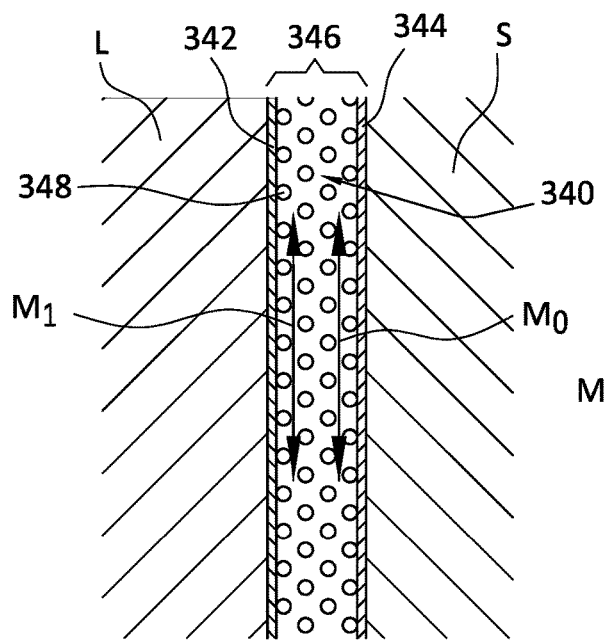
FIG. 8A is an exemplary schematic cross-sectional view of the liner, such as the liner of FIG. 1, showing a damping effect relative to a limb to a prosthetic socket.

FIG. 8A exemplifies how a lattice structure 340 of a liner of the embodiments creates a damping effect among a plurality of layers of filaments 348 between opposed sides or inner and outer layers 342, 344 of the liner. It has been found there is a "damping" effect at a thickness 346 between the opposed sides 342, 344 of the lattice structure 340, when using the liner, and is described as the difference between walking on grass (such as the embodiment of FIG. 1 and schematically shown in FIG. 8A) and walking on concrete (such as a traditional solid-walled liner).

In a traditional solid elastomeric prior art liner, the lattice structure provides damping to axial and torsional forces usually transferred directly from a hard prosthetic socket to a residual limb. The inner and outer layers of a liner can be fixed to the residual limb L and socket S, respectively. The center section 340 may allow the inner and outer layers 342, 344 to move in directions $M_I$, $M_O$, respectively, independently relative to each other to some extent without exerting high or significant shear forces on the skin. These forces are associated with skin irritation and discomfort.

Figure 8B:
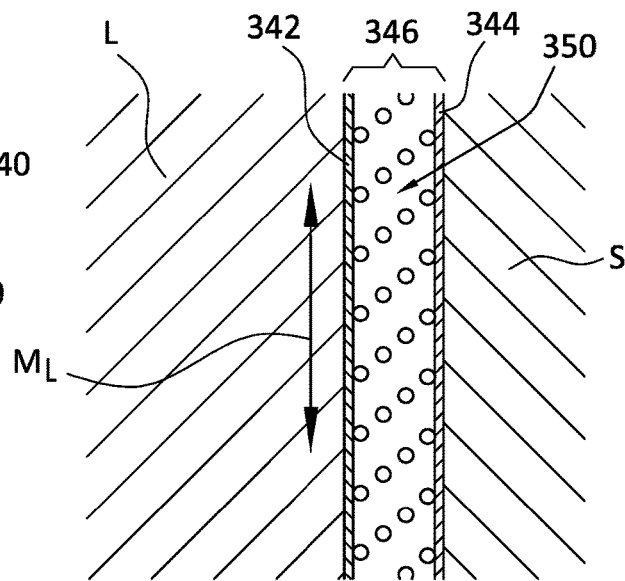
FIG. 8B is an exemplary schematic cross-sectional view of the liner, such as the liner of FIG. 1, showing volume compensation of a bony protuberance of a limb to a prosthetic socket.
Figure 8C:
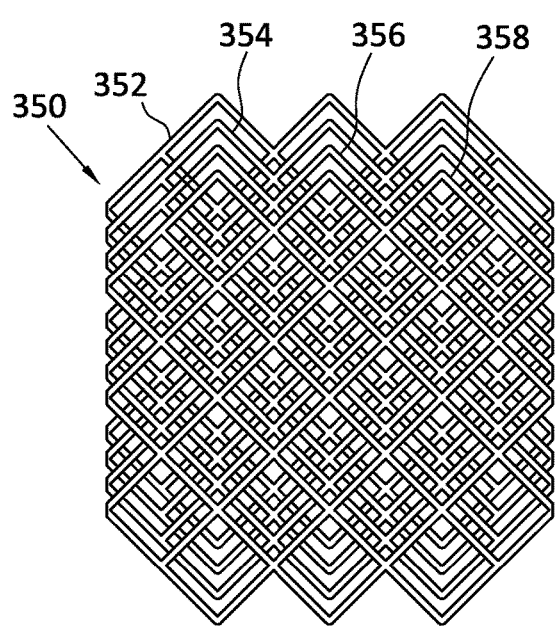
FIG. 8C is an exemplary plan view of a lattice structure according to an embodiment.

From FIG. 8B, during a stance phase in gait, there may be axial downwardly directed movement $M_L$ of the limb L from a neutral position into or toward the socket S, which may have a positive "shock-absorbing" effect. However, during a swing phase in gait, axial downwardly directed movement $M_L$ from the neutral position may cause the socket to pull away from the limb. FIG. 8C exemplifies how multiple layers 352, 354, 356, 358 of the filaments arranged in a lattice structure 350 can be aligned in such a way to promote only movement in the desired direction by inhibiting movement in the downwardly directed movement $M_L$.

Figure 9:
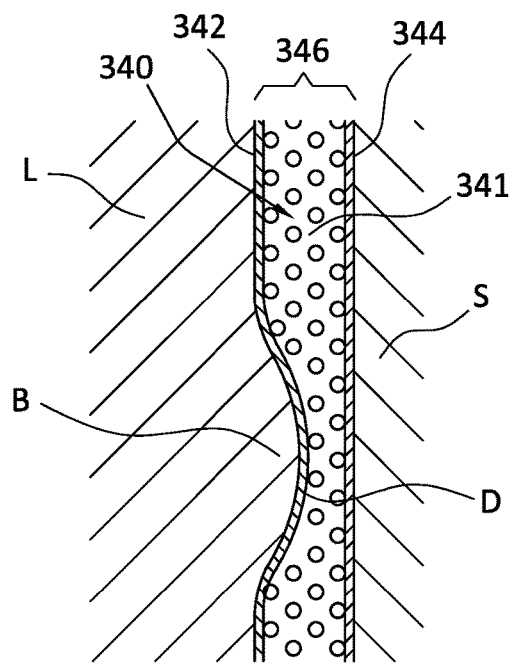
FIG. 9 is a schematic view of a layer offset variation of the liner of FIG. 1.

FIG. 9 shows how unlike in conventional liners, a lattice structure 340 has air pockets 341 that can allow the lattice structure 340 to be more easily compressed without displacing solid material and transferring pressure to another location. Residual-limb volume fluctuation is one of the main issues faced by amputees and can cause socket fit becoming too loose or uncomfortably tight. The lattice structure 340 addresses this shortcoming in known liners.

Bony prominences B on the residual limb L can cause uncomfortable pressure points. The volume-compensation characteristics of the lattice structure 340 accommodate these bony prominences on a local level, easily deforming around bony prominences B with a local deformation D, relieving localized pressure points. A solid liner, generally having a solid construction, may likewise be custom formed by including a plurality of filaments customized to a specific residual limb having bony protuberances or other irregularities creating pressure points with localized areas of the lattice structure to provide for pressure relief.

This arrangement is further beneficial because it mitigates the challenges of a user's needs or dimensions changing and rendering the liner less effective. A user whose limb changes in size due to swelling or weight changes is better accommodated by a liner according to the embodiments which does not require the additional provision of padding, recesses, or other features to accommodate the user's dimensions. Rather, the lattice structure 340 provides improved forgiveness for bony prominences, bulging, swelling, reductions thereof, and other changes in a user's dimensions owning to the improved volume-compensation characteristics.

FIG. 10A depicts an elevational view of another embodiment of a liner 200. The liner 200 may be formed from silicones or other elastomeric materials having multiple durometers. The liner 200 comprises a distal end portion 204 and a proximal portion 202, with the proximal portion 202 being open for receiving a residual limb. A liner body 203 may be formed from multiple layers of material, with an outer layer 206 having a high durometer and an inner layer 208 having a lower durometer than the outer layer 206. As with the embodiment introduced in FIG. 1, the inner and outer layers 208, 206 may define at least partially aligned interstices 210 allowing the transfer of fluid and heat from an interior portion of the liner 200.

As with previous embodiments, the liner 200 comprises a solid-walled portion 205, providing added strength and cushioning to the distal end portion 204 whereat an attachment pin or other components may attach. The solid-walled portion 205 may define a gradient 212 increasing toward the distal opening 214, with the areas immediately surrounding the distal opening 214 having increased stiffness. The increased stiffness may be due to a change in the properties of the material approaching the distal opening 214, a change in the material or of the choice of material approaching the distal opening 214, additives, or embedded structures approaching the distal opening 214, or other suitable measures.

An interface 216 may join the solid-walled portion 205 of the distal end portion 204 with the liner body 203. The liner body 203 may comprise the outer and inner layers 206, 208. A ledge, ridge or thickness 218 may be formed at the interface 216. The thickness 218 provides added mechanical strength and interfacing features with a corresponding prosthetic socket.

FIGS. 10A and 10B depict the outer layer 206 as comprising sub-layers, including first and second filaments 220, 222. The inner layer 208 may likewise comprise first and second filaments 224, 226. The first filaments 220, 224 may extend parallel to each other and perpendicularly to the second filaments 222, 226, which may extend parallel to each other. The distance by which the filaments are spaced apart from each other may define a size of interstices 210, allowing for breathability without sacrificing the mechanical advantages of a solid-walled liner.

The liner 200 may further comprise a base layer attached and adjacent to the inner layer 208. The base layer comprises a substantially solid layer of silicone perforated by a pattern of orifices corresponding at least partially to the interstices 210, as described in previous embodiments.

As described concerning the embodiment introduced in FIG. 1, the inner and outer layers 206, 208 may advantageously comprise different properties, materials, or configurations. Various durometers may be attained by providing filaments containing multiple layers of materials having different properties. The inner and outer layers 206, 208 need not have uniform properties throughout their entirety, but rather may have different properties at different locations.

In the embodiment in FIG. 10C, a cross-sectional view of a multi-layer filament 220 is depicted. The filament 220 has an inner layer 228 and an outer layer 227 concentric with and adjacent to the inner layer 228. The outer and inner layers 227, 228 may have different properties relative to one another. For example, the inner layer 228 may have a softer or lower durometer than the outer layer 227. The outer and inner layers 227, 228 may have different curing rates to facilitate chemical bonding to adjacent sub-layers or filaments. Preferably, the outer and inner layers 227, 228 are coextruded or co-deposited and are chemically bonded to one another to form a fixed and permanent integral structure of the multi-layer filament 220.

The inner layer 228 of the multi-layer filament 220 may advantageously have a different durometer relative to the filaments 224, 226 of the inner layer 208. The outer layer 227 may be formed from a material having a color profile different than a color profile or a clear color of material forming the inner layer 228. The pigments or other materials admixed with the material of outer layer 227 to define the color profile thereof may additionally provide the outer layer 227 with different properties from the inner layer 228, including a higher durometer, greater elasticity, or other properties at desired locations along with the liner. Additional layers adjacent to the outer layer 227 may be provided, or outer and inner layers 227, 228 may be provided adjacently in a laminar fashion, as examples of additional embodiments of the multi-layer filament of FIG. 10C. Any number of layers having any suitable properties may be provided in any suitable shape and at any location along a length of a filament.

According to a variation, the multi-layer filament 220 may be modified so a diameter of the cross-section of the inner layer 228 varies along the length of the filament 220. An outer diameter of the outer layer 227 may remain constant or vary, and the inner diameter of the outer layer 227 varies according to the diameter of the inner layer 228. From this variation, the multi-layer filament 220 may have varying properties according to its length due to the different properties of the outer and inner layers 227, 228.

Additional layers or structures may be included in the liner 200 to facilitate breathability, to improve the mechanical features, or to provide other functions for a liner.

Figure 11A:
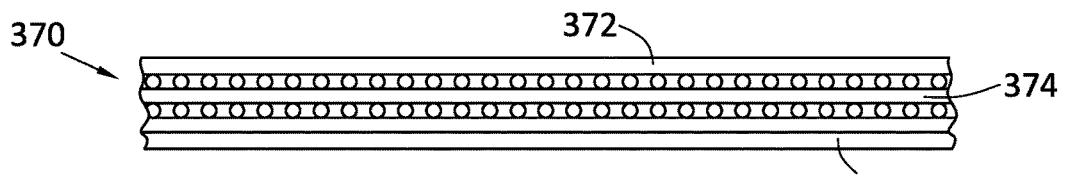
FIG. 11A is a cross-sectional view of a variation of a liner.
Figure 11B:
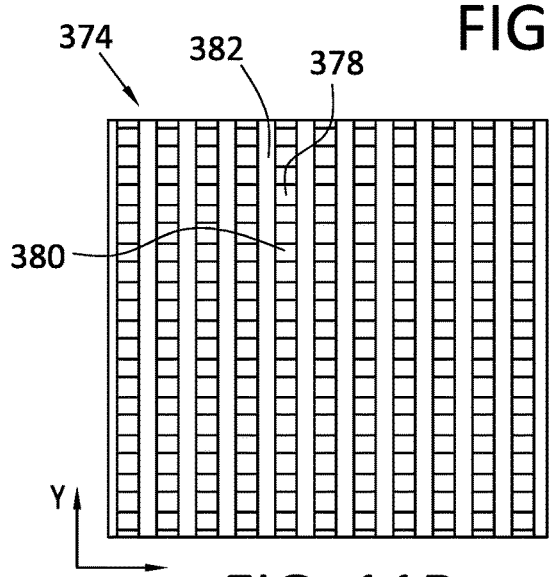
FIG. 11B is a schematic plan view of a center layer or plurality of layers in the cross-sectional view of FIG. 11A.
Figure 11C:
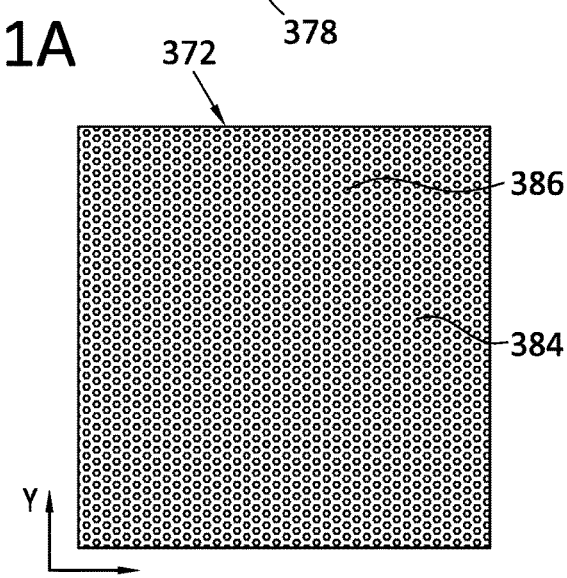
FIG. 11C is a plan view of an outer layer formed from an elastomeric material in the cross-sectional view of FIG. 11A.

FIGS. 11A-11C exemplify another embodiment 370 of a medical device such as a liner. In this embodiment, a base layer 372 is defined over a first side of a lattice structure 374 and a textile layer 378 is defined over a second side of the lattice structure 374. FIG. 11B shows how the lattice structure 374 has a grid-like structure of layers of filaments 380, 382 along the X and Y axes, respectively, with voids or cells 378 defined between or amid the generally perpendicularly arranged filaments 380, 382. Each layer 380, 382 may be stacked upon each other and aligned in the X and Y axes, or they may be staggered relative to one another, so the layers are directly above or below each cell 378, and adjacent layers may include filaments overlapping the cell 378.

FIG. 11C shows a base layer 372 having an apertured layer 384 with substantially finer apertures 386 than the lattice structure 374. The base layer 372 may be formed by a plurality of filaments forming a generally solid thickness aside from the apertures 386 and may be formed by segments of filaments in one of the X and Y directions adjacent to continuous filaments. The base layer 372 may have different material properties than the lattice structure 374, such as a substantially soft surface for facing skin of a residual limb. The apertures 386 may have a surface area lower than the cells 378, so the combined surface area of the base layer 372 is greater than the combined surface area of the apertures 386.

Figure 12A:
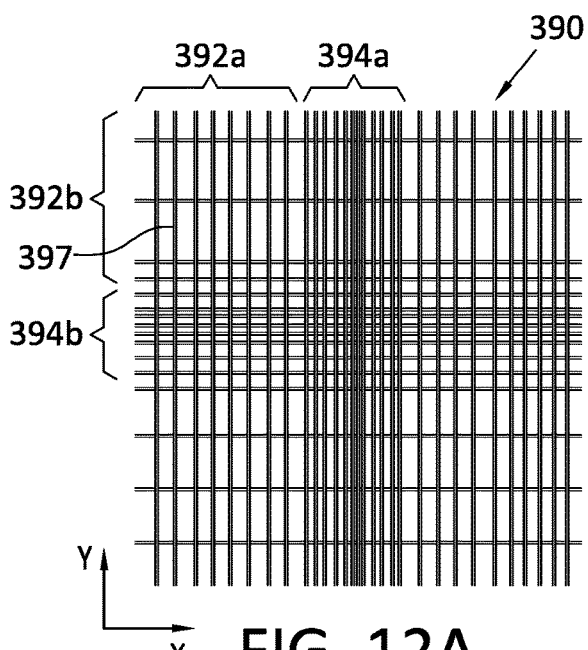
FIG. 12A is a schematic plan view of another embodiment of a layer formed from an elastomeric material.
Figure 12C:
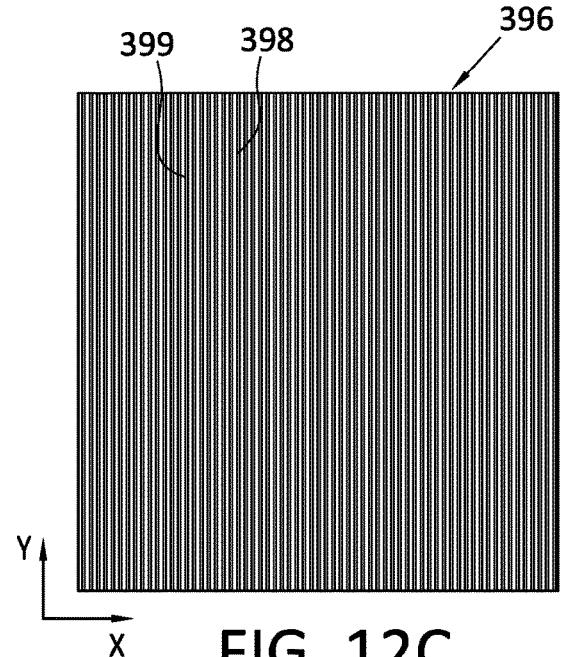
FIG. 12C is a schematic plan view of another embodiment of a layer formed from an elastomeric material.
Figure 12B:
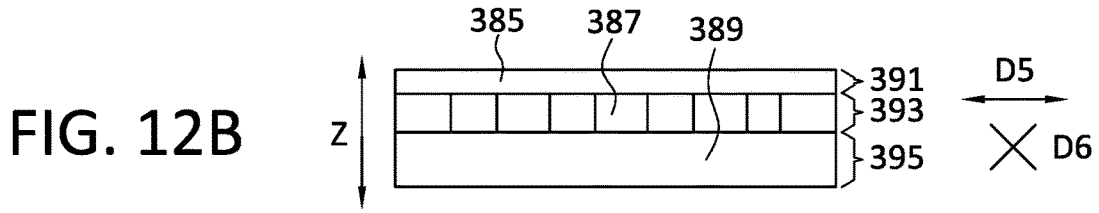
FIG. 12B is an elevational view of another embodiment of a plurality of any of the aforementioned layers.

FIG. 12A shows a variation of a lattice structure 390. In this variation, there are portions 392a, 392b of the lattice that have a generally uniform spacing of cells 397, although there may be different spacings among filaments in one direction, such as the Y direction, versus the X direction. Such relative spacings can be modified according to a desired elasticity, as mentioned referring to the embodiments of FIGS. 7A-7D. The lattice structure 390 may have localized regions where there is a gradual spacing among filaments of layers and directions, as in regions 394a, 394b. The gradual spacing may cause enhanced or minimized localized elasticity of the lattice structure 390 and may transition the lattice structure 390 from the portions 392a, 392b to a second, or other region with different properties.

FIG. 12B exemplifies how filaments 385, 387, 389 may be arranged with a different thickness in the Z-axis. For example, a first layer of filaments 385 extending in a first direction D5 have a smaller thickness 391 than a thickness 393 of a second layer of filaments 387 extending in a second direction D6, which may be orthogonal to the direction D5. A third layer of filaments 389 extending in the first direction D5 may have a greater thickness 395 than the second layer of filaments 387; however, the layers may have the same thickness as another layer. In embodiments, the filaments 385, 387, 389 may have dynamic thicknesses and diameters that change throughout the lattice structure 390. The overlap and blending of layers (for instance, at intersections between filaments of different layers or sub-layers) may be varied as suitable. Areas with larger diameters of the filaments 385, 387, 389 and/or with greater overlap and blending at the intersections of adjacent layers may have lower breathability than an area with smaller diameters of the filaments 385, 387, 389 and/or with reduced overlap between filaments of adjacent layers.

FIG. 12C exemplifies a film 396 formed from a plurality of filaments 398 arranged in the same direction, such as along a Y-axis. The plurality of filaments 398 is arranged directly adjacent to one another, so they each have a continuous and contiguous border 399 blending into one another. While shown with lines between each filament 398, in an actual sample the borders 399 among each filament 398 are indistinguishable and are not visually apparent due to the blending of the borders 399. The plurality of filaments 398 may comprise a single layer or multiple layers, whereby the borders of the filaments over the other filaments in a Z-axis likewise blend to be continuous and contiguous. The different layers of filaments may be bonded to adjacent layers of filaments in any suitable way. For instance, the attachment between layers may be continuous or may be in particular parts.

FIGS. 13A-13D illustrate another embodiment of a liner 400 having a plurality of filaments 402 defining a vertically coiled lattice structure in a direction of the Z-axis, and in X- and Y-axes. The filaments 402 are arranged adjacent one another in X and Y directions in a layer. Each filament 402a, 402b, 402c, 402d extends along the height of the thickness of the layer in the Z-axis, and interlock in the X- and Y-axes with the adjacent filaments 402, and form cells 403 in a pattern therebetween in the X, Y and Z-axes.

It has been found that vertically coiled filaments exhibit a generally consistent shape when parameters are maintained. The cells 403 vary in shape according to the shape of the coiled lattice structure. A medical device according to embodiments of the disclosure may utilize one or more layers having the plurality of filaments 402 extending in a Z-axis according to height or length of the filaments. For instance, one or more of the base, first, second, and third layers 121, 122, 124, 126 of the embodiment introduced in FIG. 1 may be formed from a plurality of filaments 402.

The filaments 402 may be arranged to utilize the phenomenon known as the liquid rope-coiling effect, so the filaments 402 may each be deposited as a linear, straight, or otherwise uncurled filament of uncured elastomeric material which can be in a liquid phase. As the linear uncured filament contacts a build surface on which the layer is being built, the liquid rope-coiling effect causes and propagates the coiling or torqued effect observed in the filaments 402. As the filaments 402 cure, solidify, and interact with adjacent filaments and the build surface, the shape of the coil is maintained.

It has been found that using the liquid rope-coiling effect to create a layer defined by the plurality of filaments 402 simplifies the manufacturing process, as a relatively short and linear filament of uncured elastomeric material may be deposited at a particular location to create a filament 402 without depositing lengthy and uninterrupted filaments in X and Y directions and with no precise depositions for any of the plurality of filaments 402, while retaining desired properties across a portion of the layer. Across the portion of the layer defined within specific lengths in the X and Y directions, the properties of the filaments and, therefore the layer such as elasticity, may average to the desired value despite varying properties of individual filaments 402.

As the filaments 402 are deposited to form a layer, the individual filaments 402 may be deposited to interlock with adjacent filaments 402 at intersections 406, 408, in which the coils of adjacent filaments 402 are intertwined. The interlocking of the filaments 402 at the intersections 406, 408 may advantageously provide properties in terms of elasticity, anisotropy, or other properties in the X and Y directions and toward the Z-axis. The interlocking of the filaments 402 at the intersections 406, 408 advantageously allows for the filaments 402 to define the layer without a backing or solid layer to which the filaments 402 are deposited or attached.

Depending on the properties of the individual filaments 402, for example, the interlocking at the intersections 406, 408 may increase the stiffness of the medical device, may facilitate extension in a desired direction, or may provide for a desired cushioning at a particular region. The adjacent filaments 402a, 402b, 402c, 402d may be chemically bonded to each other at the intersections 406, 408, as described in previous embodiments. The intersections 406, 408 may, like the properties of the individual filaments 402, have individual variation throughout the layer while still attaining a desired average property for a particular portion of the layer.

Figure 14:
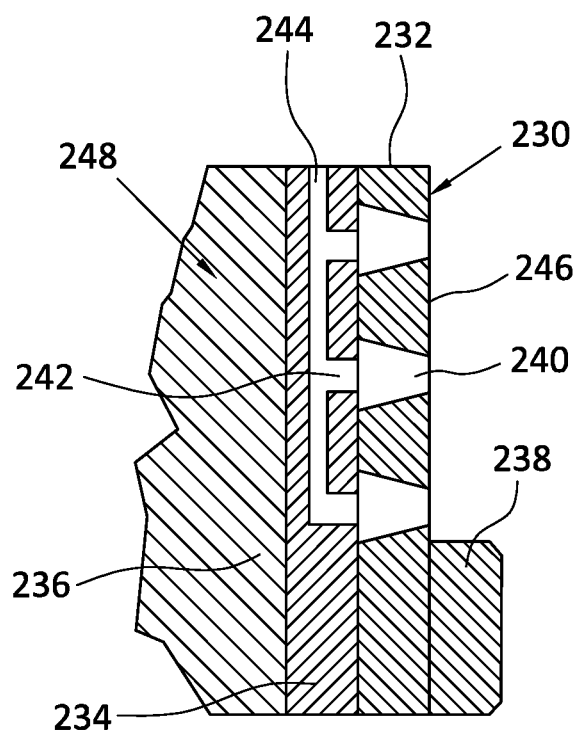
FIG. 14 is a schematic cross-sectional view of a liner according to an embodiment.

In an alternative embodiment of a portion of a liner 230 depicted in FIG. 14, the liner 230 may comprise a first layer 232, a second layer 234 adjacent to and concentric with the first layer 232, and a third layer 236 adjacent to and concentric with the second layer 234. A volume control pad or protruding feature 238 extends over portions of an inner surface 246 of the liner body and is integrally formed from the first layer 232. An uneven surface 248, such as used for vacuum sealing applications, may extend over an exterior surface of third layer 236.

Non-uniform openings 240 may be defined through a thickness of first layer 232, with outlets 242 from the non-uniform openings 240 and defined through a portion of the second layer 234 aligned with the non-uniform openings 240 and defining a vertical channel facilitating enhanced axial transfer of fluid and heat and in place of radial channels, such as along interstice axes 128 in the embodiment introduced in FIG. 1. It will be appreciated that the depicted configurations, sizes, patterns, materials, properties, and numbers of openings, channels, layers, and other features in the depicted embodiments are exemplary, and other configurations of features and structures may achieve a medical device according to the disclosure.

Figure 15:
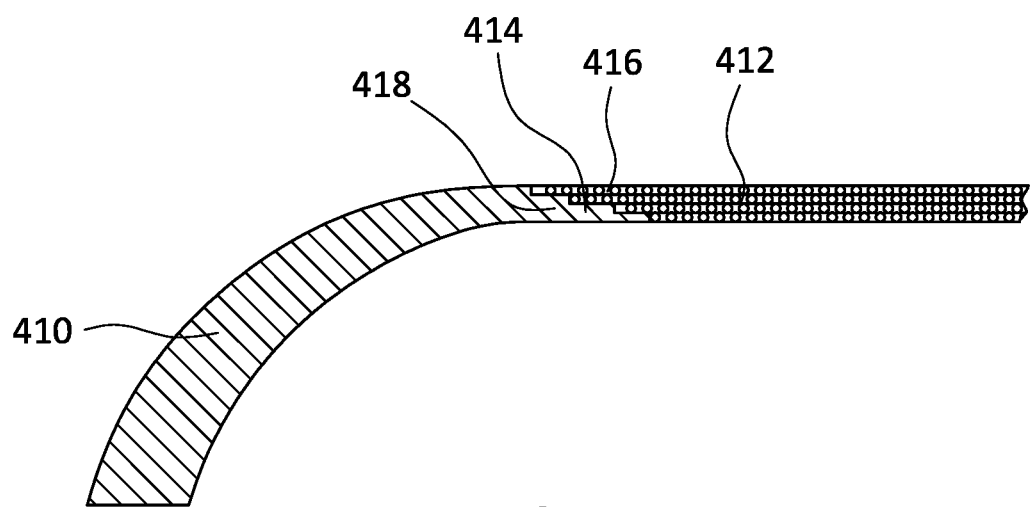
FIG. 15 is a schematic cross-sectional view of an interface of at least one layer and a distal cup in the liner of FIG. 1.

FIG. 15 exemplifies how the thickness of a lattice structure 412 according to embodiments of the disclosure may have a tapered or stepped profile to interlock with a distal end 410 of a liner, as shown in FIG. 1. The distal end 410 may be a solid-wall construction formed from discrete filaments and may be formed from an elastomeric or polymeric material different from the lattice structure 412. According to the depicted embodiment, an interface 414 between a stepped end portion 416 of the lattice structure 412 and a corresponding stepped end portion 418 of the distal end 410 may be continuous and contiguous with both end portions 416, 418 blending to form a chemical bond.

In an embodiment, the ventilated structure 110 and solid-walled structure 112 of the embodiment of FIG. 1 could be formed with inverse tapers at the interface 108. An embodiment is illustrated in FIG. 15. The solid-walled structure 418 defining the stepped end portion of the distal end 410 decreases in thickness at the interface 414. The solid-walled structure 418 at the interface 414 is structured near the interior surface I of the liner. The thickness of the ventilated structure 416 defining the stepped end portion of the lattice structure 412 increases at the interface 414 until it has reached the desired thickness. The ventilated structure 416 at the interface 414 is structured near the exterior surface E of the liner. This feature is advantageous because it reduces pressure points at the interface 414 between the ventilated structure 416 and the solid-walled structure 418. This embodiment provides a larger surface area for the interface 414, which ensures a stronger and more durable bond between the ventilated structure 416 and the solid-walled structure 418.

In a variation, the solid-walled structure 418 and the ventilated structure 416 taper at the interface 414 as described above. However, in this embodiment, the solid-walled structure 418 at the interface 414 is structured near the exterior surface E of the liner. Inversely, the ventilated structure 416 at the interface 414 is structured near the interior surface I of the liner. This feature is advantageous because it extends the ventilating structure 416 further down into the distal end 410 providing better wicking of heat and fluid from the distal end 410. The tapering of the interface 414 can be increased or decreased from the taper demonstrated in FIG. 15, increasing or decreasing the reach of the ventilated structure 416 into the distal end 410. This may also cushion the limb against pressure points because of the features of a lattice structure as described herein.

The stepped interface 414 between the solid-walled structure 418 and the ventilated structure 416 advantageously provides a gradual change in compression. A compression profile is smoother and reduced as the solid-walled structure 418 gradually transitions via the stepped interface 414 into the ventilated structure 416.

Figure 16:
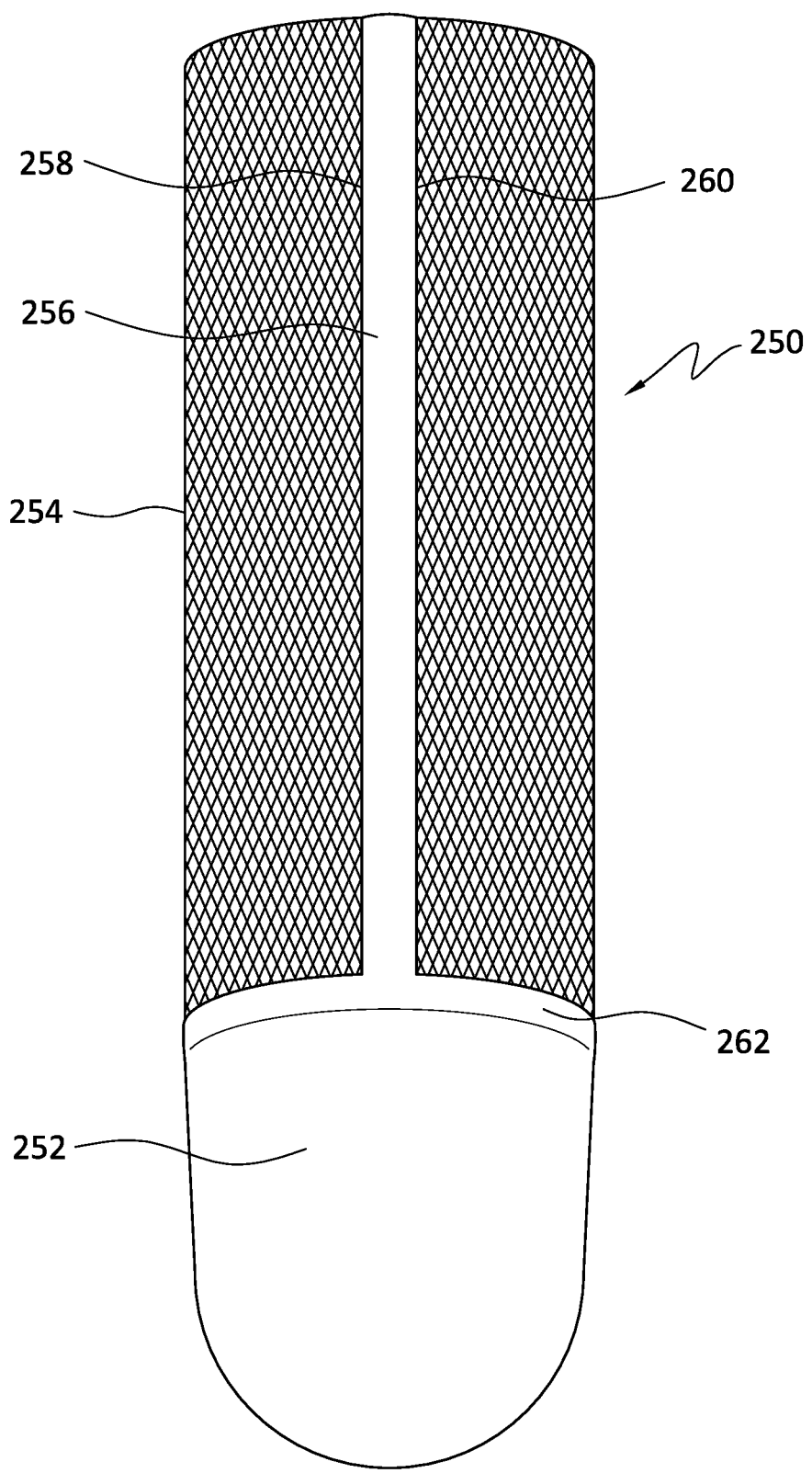
FIG. 16 is a perspective view of another liner embodiment.

In another embodiment of a liner 250 depicted in FIG. 16, the liner 250 includes a liner body 252 at a distal end of the liner 250, with a textile 254 covering a portion of the liner body 252 proximally of the distal end and attaching at a seam or seal 256. The textile 254 may be discretized from the distal end by a distal seam 262 at which the textile 254 is reinforcedly bonded to the liner body 252. First and second edges 258, 260 of the textile cover 254 are advantageously joined using the material forming the liner body 252.

In contrast to existing prosthetic liners in which textile covers must be joined at a seam using stitching, sewing, or other attachment means, which increase the costs and complexities of manufacturing liners, the textile 254 may be joined at the first and second edges 258, 260 by attaching or impregnating the textile 254 with the elastomer forming the liner body 252.

The liner 250 may comprise throughout an entirety of the liner body 252 a matrix arranged for limiting axial elongation while allowing circumferential or radial elongation, this arrangement advantageously mitigating "pistoning," "milking," and other undesirable effects between a liner and residual limb. The liner body 252 may comprise layers of filaments or other materials arranged to receive the matrix.

By providing a medical device according to embodiments described, the problems of medical devices such as liners poorly navigating the tension between mechanical strength needed to cushion and protect a body portion such as a residual limb and the need for a breathable device to mitigate the buildup of fluid and heat are addressed. The structures forming layers, multi-layer filaments, and openings and structures defined advantageously provide for permeability of the liner to fluid and heat while retaining needed structural strength to cushion the residual limb. The liner further provides for simplified manufacturing processes by incorporating the stitching or sewing of a textile cover in the material forming the layers or liner body.

The embodiments of a liner further provide for a multi-layer liner structure with layers and sub-layers that comprise different materials and/or properties for providing a liner with properly arranged portions having mechanical strength, elasticity, comfort features, frictional features, and stiffness.

It is to be understood that not necessarily all objects or advantages may be achieved under any embodiment of the disclosure. Those skilled in the art will recognize that the medical device may be embodied or carried out, so it achieves or optimizes one advantage or group of advantages as taught herein without achieving other objects or advantages as taught or suggested herein.

The skilled artisan will recognize the interchangeability of various disclosed features. Besides the variations described, other known equivalents for each feature can be mixed and matched by one of skill in this art to construct a medical device under principles of the present disclosure. It will be understood by the skilled artisan that the features described may apply to other types of orthopedic, prosthetic, or medical devices.

Although this disclosure describes certain exemplary embodiments and examples of a medical device or liner, it nevertheless will be understood by those skilled in the art that the present disclosure extends beyond the specifically disclosed prosthetic socket embodiments to other alternative embodiments and/or users of the disclosure and obvious modifications and equivalents thereof. It is intended that the present disclosure should not be limited by the particular disclosed embodiments described above, and may be extended to medical devices and supports, and other applications that may employ the features described.

The invention claimed is:

1. A prosthetic liner defining a proximal end and a distal end, and a liner body defined between the proximal end and distal end, and having a tubular shape, the liner comprising:
   a lattice structure defined as a plurality of layers monolithically formed as an inseparable and continuous structure;
   wherein the lattice structure having a first layer of first filaments discretely formed from and consisting a silicone material, and overlapping a second layer of second filaments discretely formed from and consisting the silicone material, the first and second filaments of the first and second layers, respectively, overlapping and securing to one another at discrete intersections to form a first set of interstices located therebetween in a predetermined pattern, wherein the first filaments are parallel to and spaced apart from each other, and extend in a first direction oriented differently from a second direction in which the second filaments extend;
   wherein the first and second layers of the first and second filaments are directly adjacent, and permanently and chemically bonded to one another at the discrete intersections, the first and second layers are blended at least in part with one another in a blended region at an interface of the first and second layers, the blended region forming a permanent chemical bond in which the silicone material of the first and second layers of the first and second filaments intermix.

2. The prosthetic liner of claim 1, wherein the first layer of the first filaments are arranged at an angle at or greater than 0 degrees and at or less than 90 degrees relative to the second layer of the second filaments.

3. The prosthetic liner of claim 1, wherein the lattice structure includes a third layer of third filaments, consisting and discretely formed from the silicone material, the third layer of third filaments located on an opposite side of the second layer of the second filaments from the first layer of the first filaments and offset at an angle at or greater than 0 degrees and at or less than 90 degrees relative to the first layer of the first filaments.

4. The prosthetic liner of claim 3, wherein each of the third filaments of the third layer are parallel to each of the first filaments of the first layer of the first filaments.

5. The prosthetic liner of claim 1, further comprising a base layer formed from a plurality of first base-layer filaments formed from another silicone material and directly adjacent to one another without interruption and defining a continuous sheet, the plurality of first base-layer filaments blending into one another to form a continuous and contiguous border, the base layer permanently secured to an inner side of the first layer of filaments by being chemically bonded to said first layer of filaments, the base layer forming a substantially solid film of the another silicone material and a solid surface area.

6. The prosthetic liner of claim 5, wherein the base layer defines a plurality of apertures formed from shortened segments of second base-layer filaments formed from the another silicone and directly adjacent without interruption to the first base-layer filaments, the first and second base-layer filaments being permanently and chemically bonded to one another.

7. The prosthetic liner of claim 6, wherein individual apertures of the plurality of apertures of the base layer are sized substantially smaller than the interstices of the lattice structure, and are in correspondence with the interstices of the lattice structure.

8. The prosthetic liner of claim 5, wherein the base layer is concentric to the first layer.

9. The prosthetic liner of claim 5, wherein the another silicone material is different from the silicone material forming the first layer, and includes at least silicone oil.

10. The prosthetic liner of claim 1, wherein the distal end has a closed configuration and the proximal end has an open configuration, wherein the liner body is provided with an interface between the distal end and the proximal end whereat the silicone material of the first layer and elastomeric material of the distal end are chemically bonded to one another.

11. The prosthetic liner of claim 10, wherein the interface comprises a blend of the silicone material of the first layer and the elastomeric material of the distal end.

12. The prosthetic liner of claim 10, wherein the distal end is formed by at least one distal layer defined by elastomeric filaments directly adjacent to one another without interruption so that the distal end is vapor- and liquid-impermeable.

13. The prosthetic liner of claim 12, wherein the distal end forms a concave structure bordering the interface and defined by the at least one distal layer.

14. The prosthetic liner of claim 12, wherein an entirety of a thickness of the distal end is formed by the at least one distal layer.

15. The prosthetic liner of claim 1, further comprising a textile layer secured to an outer side of the lattice structure, the textile layer integrally secured to the lattice structure with the silicone material associated with at least one of the first and second layers mechanically interlocking with the textile layer.

16. The prosthetic liner of claim 1, wherein each of the first filaments of the first layer and each the second filaments of the second layer have a uniform cross-section extending along its length in a predetermined shape;
   wherein the predetermined shape is selected from the group consisting of square, rectangle, triangle, circle, or circular oval.

17. The prosthetic liner of claim 1, wherein each of the first filaments of the first layer and each of the second filaments of the second layer have an asymmetric cross-section extending along its length.

18. A medical device, comprising:
   a lattice structure defined as a plurality of layers monolithically formed as an inseparable and continuous structure;

wherein the lattice structure includes a first layer of first filaments discretely formed from and consisting a medical-grade silicone material and overlapping a second layer of second filaments discretely formed from and consisting the medical-grade silicone material, the first and second filaments of the first and second layers, respectively, overlapping each other in a predetermined pattern at discrete intersections, the first and second filaments of the first and second layers, respectively, overlapping and forming a first set of interstices located therebetween in a predetermined pattern, wherein the first filaments are parallel to and spaced apart from each other, and extend in a first direction oriented differently from a second direction in which the second filaments extend;

wherein the first and second layers of the first and second filaments are directly adjacent and permanently chemically bonded to one another at the discrete intersections and blended at least in part with one another in a blended region among the first and second filaments, the blended region forming a permanent chemical bond in which the medical-grade silicone material of the first and second layers of the first and second filaments intermix;

wherein the first filaments are arranged at an angle at or greater than 0 degrees and at or less than 90 degrees relative to the second filaments.

19. A prosthetic liner defining first or proximal and second or distal ends and a liner body defined therebetween, comprising:

a lattice structure defined as a plurality of layers monolithically formed as an inseparable and continuous structure;

wherein the lattice structure includes a first layer of first filaments discretely formed from at least one elastomeric material and overlapping a second layer of second filaments discretely formed from at least one elastomeric material, the first and second filaments of the first and second layers, respectively, overlapping at discrete intersections and forming a first set of interstices located therebetween in a predetermined pattern, wherein the first filaments are parallel to and spaced apart from each other, and extend in a first direction oriented differently from a second direction in which the second filaments extend;

wherein the first and second layers of the first and second filaments are directly adjacent, and permanently and chemically bonded to one another at the discrete intersections, the first and second layers are blended at least in part with one another in a blended region at an interface of the first and second layers, the blended region forming a permanent chemical bond in which the first and second layers of the first and second filaments intermix;

a base layer formed from a plurality of first base-layer filaments directly adjacent to one another without interruption and defining a continuous sheet, the plurality of first base-layer filaments blending into one another to form a continuous and contiguous border, the base layer secured to an inner side of the first layer of filaments, the base layer forming a substantially solid film of elastomeric material and a solid surface area;

wherein the base layer defines a plurality of apertures formed from shortened segments of second base-layer filaments directly adjacent without interruption to the first base-layer filaments, the first and second base-layer filaments are chemically bonded to one another;

wherein individual apertures of the plurality of apertures of the base layer are sized substantially smaller than the interstices of the lattice structure, and are in correspondence with the interstices of the lattice structure.

20. The prosthetic liner of claim 19, wherein the at least one elastomeric material of the first and second filaments of the lattice structure is a first medical grade silicone.

21. The prosthetic liner of claim 20, wherein the base layer including the first and second base-layer filaments is formed from a second medical grade silicone.

22. The prosthetic liner of claim 21, wherein the second medical grade silicone includes a silicone oil.

\* \* \* \* \*